US008785161B2

(12) United States Patent
Rybak et al.

(10) Patent No.: US 8,785,161 B2
(45) Date of Patent: *Jul. 22, 2014

(54) METHOD FOR PRODUCING L-AMINO ACIDS USING BACTERIA OF THE ENTEROBACTERIACEAE FAMILY

(75) Inventors: Konstantin Vyacheslavovich Rybak, Moscow (RU); Ekaterina Aleksandrovna Slivinskaya, Moscow (RU); Ekaterina Alekseevna Savrasova, Moscow (RU); Valeriy Zavenovich Akhverdian, Moscow (RU); Elena Vitalievna Klyachko, Moscow (RU); Sergei Vladimirovich Mashko, Moscow (RU); Vera Georgievna Doroshenko, Moscow (RU); Larisa Gotlibovna Airikh, Moscow region (RU); Tatyana Viktorovna Leonova, Moscow (RU); Mikhail Markovich Gusyatiner, Moscow (RU); Elvira Borisovna Voroshilova, Moscow (RU); Yury Ivanovich Kozlov, Moscow (RU); Yoshihiko Hara, Kawasaki (JP); Takuji Ueda, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/466,266

(22) Filed: May 8, 2012

(65) Prior Publication Data
US 2012/0219996 A1 Aug. 30, 2012

Related U.S. Application Data

(60) Division of application No. 13/032,057, filed on Feb. 22, 2011, which is a continuation of application No. 11/247,138, filed on Oct. 12, 2005, now Pat. No. 7,915,018.

(60) Provisional application No. 60/673,807, filed on Apr. 22, 2005.

(30) Foreign Application Priority Data

Oct. 22, 2004 (RU) ................................ 2004130954

(51) Int. Cl.
*C12P 13/04* (2006.01)
*C12P 13/08* (2006.01)

(52) U.S. Cl.
USPC ..... 435/106; 435/115; 435/69.1; 435/252.33; 530/350

(58) Field of Classification Search
IPC ............................................ C12P 13/04,13/08
See application file for complete search history.

(56) References Cited

U.S. PATENT DOCUMENTS

| | | | |
|---|---|---|---|
| 4,278,765 | A | 7/1981 | Debabov et al. |
| 4,346,170 | A | 8/1982 | Sano et al. |
| 5,175,107 | A | 12/1992 | Debabov et al. |
| 5,376,538 | A | 12/1994 | Kino et al. |
| 5,474,918 | A | 12/1995 | Kino et al. |
| 5,602,030 | A | 2/1997 | Ingrahm et al. |
| 5,661,012 | A | 8/1997 | Sano et al. |
| 5,705,371 | A | 1/1998 | Debabov et al. |
| 5,939,307 | A | 8/1999 | Wang et al. |
| 6,040,160 | A | 3/2000 | Kojima et al. |
| 6,297,031 | B1 | 10/2001 | Debabov et al. |
| 6,960,455 | B2 | 11/2005 | Livshits et al. |
| 7,138,266 | B2 | 11/2006 | Debabov et al. |
| 7,179,623 | B2 | 2/2007 | Livshits et al. |
| 7,186,531 | B2 | 3/2007 | Akhverdian et al. |
| 7,259,003 | B2 | 8/2007 | Livshits et al. |
| 7,300,786 | B2 | 11/2007 | Klyachko et al. |
| 7,306,933 | B2 | 12/2007 | Dien et al. |
| 7,344,874 | B2 | 3/2008 | Hara et al. |
| 7,381,548 | B2 | 6/2008 | Sheremet'eva et al. |
| 7,399,618 | B2 | 7/2008 | Klyachko et al. |
| 7,422,880 | B2 | 9/2008 | Rybak et al. |
| 7,470,524 | B2 | 12/2008 | Rybak et al. |
| 7,476,531 | B2 | 1/2009 | Tabolina et al. |
| 7,501,282 | B2 | 3/2009 | Hara et al. |
| 7,531,332 | B2 | 5/2009 | Livshits et al. |
| 7,547,531 | B2 | 6/2009 | Kataoka et al. |
| 7,604,979 | B2 | 10/2009 | Katashkina et al. |
| 7,618,803 | B2 | 11/2009 | Tabolina et al. |

(Continued)

FOREIGN PATENT DOCUMENTS

| | | |
|---|---|---|
| EP | 0 219 027 | 4/1987 |
| EP | 0 301 572 | 2/1989 |
| EP | 1 013 765 | 6/2000 |
| EP | 1 149 911 | 10/2001 |
| EP | 1 157 396 | 11/2001 |
| JP | S60-47692 | 3/1985 |
| JP | 2004-254694 | 9/2004 |
| WO | WO01/14525 | 3/2001 |

OTHER PUBLICATIONS

S. Song et al. "Organization and Regulation of the D-Xylose Operons in *Escherichiacoli* K-12: XylR Acts as a Transcriptional Activator", J. Bacteriology 179(22):7025-7032. (1997).*
Chen, H., et al., "Determination of the Optimal Aligned Spacing Between the Shine-Dalgarno Sequence and the Translation Initiation Codon of *Escherichia coli* mRNAs," Nuc. Acids Res. 1994;22(23):4953-4957.
Cheng, G., et al., Digest of the World Latest Medical Information; vol. 3, No. 3:pp. 1121-1124 and 1142 (2004).

(Continued)

*Primary Examiner* — Rebecca Prouty
(74) *Attorney, Agent, or Firm* — Shelly Guest Cermak; Cermak Nakajima LLP

(57) ABSTRACT

There is disclosed a method for producing L-amino acid, for example L-threonine, L-lysine, L-histidine, L-phenylalanine, L-arginine or L-glutamic acid, using a bacterium of the Enterobacteriaceae family, wherein the bacterium has been modified to enhance an activity of D-xylose permease.

8 Claims, 1 Drawing Sheet

(56) References Cited

U.S. PATENT DOCUMENTS

| | | | |
|---|---|---|---|
| 7,618,804 B2 | 11/2009 | Tabolina et al. | |
| 7,629,142 B2 | 12/2009 | Ueda et al. | |
| 7,771,976 B2 | 8/2010 | Gulevich et al. | |
| 7,785,845 B2 | 8/2010 | Hara et al. | |
| 7,785,858 B2 | 8/2010 | Kozlov et al. | |
| 7,785,860 B2 | 8/2010 | Klyachko et al. | |
| 7,794,988 B2 | 9/2010 | Filippov et al. | |
| 7,803,584 B2 | 9/2010 | Rybak et al. | |
| 7,811,798 B2 | 10/2010 | Rybak et al. | |
| 7,820,415 B2 | 10/2010 | Gulevich et al. | |
| 7,833,762 B2 | 11/2010 | Kataoka et al. | |
| 7,855,060 B2 | 12/2010 | Filippov et al. | |
| 7,871,801 B2 | 1/2011 | Ueda et al. | |
| 7,888,077 B2 | 2/2011 | Filippov et al. | |
| 8,003,367 B2 * | 8/2011 | Marchenko et al. | 435/252.33 |
| 8,003,368 B2 | 8/2011 | Marchenko et al. | |
| 2002/0040129 A1 | 4/2002 | Mockel et al. | |
| 2003/0148473 A1 | 8/2003 | Livshits et al. | |
| 2004/0038380 A1 | 2/2004 | Debabov et al. | |
| 2004/0132165 A1 | 7/2004 | Akhverdian et al. | |
| 2004/0229320 A1 | 11/2004 | Stoynova et al. | |
| 2004/0229321 A1 | 11/2004 | Savrasova et al. | |
| 2005/0048631 A1 | 3/2005 | Klyachko et al. | |
| 2005/0054061 A1 | 3/2005 | Klyachko et al. | |
| 2005/0124048 A1 | 6/2005 | Akhverdian et al. | |
| 2005/0124049 A1 | 6/2005 | Ziyatdinov et al. | |
| 2005/0176033 A1 | 8/2005 | Klyachko et al. | |
| 2005/0181488 A1 | 8/2005 | Akhverdian et al. | |
| 2005/0191684 A1 | 9/2005 | Zimenkov et al. | |
| 2005/0196846 A1 | 9/2005 | Hara et al. | |
| 2005/0214911 A1 | 9/2005 | Marchenko et al. | |
| 2005/0214913 A1 | 9/2005 | Marchenko et al. | |
| 2005/0239175 A1 | 10/2005 | Tabolina et al. | |
| 2006/0014257 A1 | 1/2006 | Katashkina et al. | |
| 2006/0035346 A1 | 2/2006 | Savrasova et al. | |
| 2006/0035348 A1 | 2/2006 | Gulevich et al. | |
| 2006/0088919 A1 | 4/2006 | Rybak et al. | |
| 2008/0241888 A1 | 10/2008 | Zakataeva et al. | |
| 2009/0087886 A1 | 4/2009 | Filippov et al. | |
| 2009/0104667 A1 | 4/2009 | Asakura et al. | |
| 2009/0117623 A1 | 5/2009 | Marchenko et al. | |
| 2009/0137010 A1 | 5/2009 | Shakulov et al. | |
| 2009/0137011 A1 | 5/2009 | Filippov et al. | |
| 2009/0148915 A1 | 6/2009 | Van Dien et al. | |
| 2009/0155861 A1 | 6/2009 | Rybak et al. | |
| 2009/0203090 A1 | 8/2009 | Ptitsyn et al. | |
| 2009/0209011 A1 | 8/2009 | Rybak et al. | |
| 2009/0215131 A1 | 8/2009 | Hara et al. | |
| 2009/0226919 A1 | 9/2009 | Gulevich et al. | |
| 2009/0239267 A1 | 9/2009 | Rybak et al. | |
| 2009/0269819 A1 | 10/2009 | Filippov et al. | |
| 2009/0275089 A1 | 11/2009 | Klyachko et al. | |
| 2009/0275090 A1 | 11/2009 | Ueda et al. | |
| 2009/0275092 A1 | 11/2009 | Kodera et al. | |
| 2009/0286290 A1 | 11/2009 | Hara et al. | |
| 2010/0047878 A1 | 2/2010 | Nagai et al. | |
| 2010/0062496 A1 | 3/2010 | Takikawa et al. | |
| 2010/0112647 A1 | 5/2010 | Hara et al. | |
| 2010/0143982 A1 | 6/2010 | Filippov et al. | |
| 2010/0143983 A1 | 6/2010 | Kiryukhin et al. | |
| 2010/0184162 A1 | 7/2010 | Imaizumi et al. | |
| 2010/0190217 A1 | 7/2010 | Doi et al. | |
| 2010/0267094 A1 | 10/2010 | Kozlov et al. | |
| 2010/0279362 A1 | 11/2010 | Rybak et al. | |
| 2010/0311129 A1 | 12/2010 | Rybak et al. | |
| 2011/0177566 A1 | 7/2011 | Savrasova et al. | |

OTHER PUBLICATIONS

Davis, E. O., et al., "The Cloning and DNA Sequence of the Gene *xylE* for Xylose-Proton Symport in *Escherichia coli* K12," J. Biol. Chem. 1987;262(29):13928-13932.

GenBank NC_000913 nucleotides from 2500001-2510000 (Oct. 2001).

Griffith, J. K., et al., "Membrane transport proteins: implication of sequence comparisons," Curr. Op. Cell Biol. 1992;4:684-695.

Healy, F. G., et al., "Development of ethanologenic *Escherichia coli* for the simultaneous utilization of glucose and xylose," Abstracts of the General Meeting of the American Society for Microbiology, 101st General Meeting of the American Society for Microbiology, Orlando, FL, USA; May 20-24, 2001, vol. 101, p. 536.

Lam, V. M. S., et al., "Proton-Linked D-Xylose Transport in *Escherichia coli*," J. Bacteriol. 1980;143(1):396-402.

Li, K., et al., "Microbial Synthesis of 3-Dehydroshikimic Acid: A Comparative Analysis of D-Xylose, L-Arabinose, and D-Glucose Carbon Sources," Biotechnol. Progress 1999;15:876-883.

Livshits, V. A., et al., "Investigation of the relA Gene Function in the Expression of Amino Acid Operons," Genetika 1978;14(6):947-956.

Sumiya, M., et al., "Molecular Genetics of a Receptor Protein for D-Xylose, Encoded by the Gene *xylF*, in *Escherichia coli*," Receptors and Channels 1995;3:117-128.

Wovcha, M. G., et al., "Amplification of D-Xylose and D-Glucose Isomerase Activities in *Escherichia coli* by Gene Cloning," App. Environmen. Microbiol. 1983;45(4):1402-1404.

International Search Report and Written Opinion of the International Searching Authority for PCT App. No. PCT/JP2005/019840 (Mar. 13, 2006).

International Preliminary Report on Patentability for PCT App. No. PCT/JP2005/019840 (May 3, 2007).

Office Action from Chinese Patent App. No. 200580036221.3 (May 22, 2009) with English translation thereof.

Communication Pursuant to Article 94(3) EPC for EP Patent App. No. 05805329.9 (Apr. 12, 2010).

Genbank, Accession No. NP_290665.1, xylose-proton symport [*Escherichia coli* O157:H7 EDL933], Sep. 27, 2001.

Office Action for Chinese Patent App. No. 201110271264.7 (Jan. 6, 2013) with English translation thereof.

Non-Final Office Action from co-pending U.S. Appl. No. 13/032,057 (Oct. 18, 2012).

* cited by examiner

SEQUENCE LISTING

<160> NUMBER OF SEQ ID NOS: 14

<210> SEQ ID NO 1
<211> LENGTH: 1476
<212> TYPE: DNA
<213> ORGANISM: Escherichia coli
<220> FEATURE:
<221> NAME/KEY: CDS
<222> LOCATION: (1)..(1476)

<400> SEQUENCE: 1

```
atg aat acc cag tat aat tcc agt tat ata ttt tcg att acc tta gtc    48
Met Asn Thr Gln Tyr Asn Ser Ser Tyr Ile Phe Ser Ile Thr Leu Val
1               5                   10                  15 gct aca tta ggt ggt tta tta ttt ggc tac gac acc gcc gtt att tcc    96
Ala Thr Leu Gly Gly Leu Leu Phe Gly Tyr Asp Thr Ala Val Ile Ser
            20                  25                  30 ggt act gtt gag tca ctc aat acc gtc ttt gtt gct cca caa aac tta   144
Gly Thr Val Glu Ser Leu Asn Thr Val Phe Val Ala Pro Gln Asn Leu
        35                  40                  45 agt gaa tcc gct gcc aac tcc ctg tta ggg ttt tgc gtg gcc agc gct   192
Ser Glu Ser Ala Ala Asn Ser Leu Leu Gly Phe Cys Val Ala Ser Ala
    50                  55                  60 ctg att ggt tgc atc atc ggc ggt gcc ctc ggt ggt tat tgc agt aac   240
Leu Ile Gly Cys Ile Ile Gly Gly Ala Leu Gly Gly Tyr Cys Ser Asn
65                  70                  75                  80 cgc ttc ggt cgt cgt gat tca ctt aag att gct gct gtc ctg ttt ttt   288
Arg Phe Gly Arg Arg Asp Ser Leu Lys Ile Ala Ala Val Leu Phe Phe
                85                  90                  95 att tct ggt gta ggt tct gcc tgg cca gaa ctt ggt ttt acc tct ata   336
Ile Ser Gly Val Gly Ser Ala Trp Pro Glu Leu Gly Phe Thr Ser Ile
```

```
                100                 105                 110
aac ccg gac aac act gtg cct gtt tat ctg gca ggt tat gtc ccg gaa    384
Asn Pro Asp Asn Thr Val Pro Val Tyr Leu Ala Gly Tyr Val Pro Glu
            115                 120                 125 ttt gtt att tat cgc att att ggc ggt att ggc gtt ggt tta gcc tca    432
Phe Val Ile Tyr Arg Ile Ile Gly Gly Ile Gly Val Gly Leu Ala Ser
130                 135                 140 atg ctc tcg cca atg tat att gcg gaa ctg gct cca gct cat att cgc    480
Met Leu Ser Pro Met Tyr Ile Ala Glu Leu Ala Pro Ala His Ile Arg
        145                 150                 155                 160 ggg aaa ctg gtc tct ttt aac cag ttt gcg att att ttc ggg caa ctt    528
Gly Lys Leu Val Ser Phe Asn Gln Phe Ala Ile Ile Phe Gly Gln Leu
                165                 170                 175 tta gtt tac tgc gta aac tat ttt att gcc cgt tcc ggt gat gcc agc    576
Leu Val Tyr Cys Val Asn Tyr Phe Ile Ala Arg Ser Gly Asp Ala Ser
            180                 185                 190 tgg ctg aat act gac ggc tgg cgt tat atg ttt gcc tcg gaa tgt atc    624
Trp Leu Asn Thr Asp Gly Trp Arg Tyr Met Phe Ala Ser Glu Cys Ile
                195                 200                 205 cct gca ctg ctg ttc tta atg ctg ctg tat acc gtg cca gaa agt cct    672
Pro Ala Leu Leu Phe Leu Met Leu Leu Tyr Thr Val Pro Glu Ser Pro
        210                 215                 220 cgc tgg ctg atg tcg cgc ggc aag caa gaa cag gcg gaa ggt atc ctg    720
Arg Trp Leu Met Ser Arg Gly Lys Gln Glu Gln Ala Glu Gly Ile Leu
225                 230                 235                 240 cgc aaa att atg ggc aac acg ctt gca act cag gca gta cag gaa att    768
Arg Lys Ile Met Gly Asn Thr Leu Ala Thr Gln Ala Val Gln Glu Ile
                245                 250                 255 aaa cac tcc ctg gat cat ggc cgc aaa acc ggt ggt cgt ctg ctg atg    816
Lys His Ser Leu Asp His Gly Arg Lys Thr Gly Gly Arg Leu Leu Met
            260                 265                 270 ttt ggc gtg ggc gtg att gta atc ggc gta atg ctc tcc atc ttc cag    864
Phe Gly Val Gly Val Ile Val Ile Gly Val Met Leu Ser Ile Phe Gln
        275                 280                 285 caa ttt gtc ggc atc aat gtg gtg ctg tac tac gcg ccg gaa gtg ttc    912
Gln Phe Val Gly Ile Asn Val Val Leu Tyr Tyr Ala Pro Glu Val Phe
                290                 295                 300 aaa acg ctg ggg gcc agc acg gat atc gcg ctg ttg cag acc att att    960
Lys Thr Leu Gly Ala Ser Thr Asp Ile Ala Leu Leu Gln Thr Ile Ile
305                 310                 315                 320 gtc gga gtt atc aac ctc acc ttc acc gtt ctg gca att atg acg gtg   1008
Val Gly Val Ile Asn Leu Thr Phe Thr Val Leu Ala Ile Met Thr Val
                325                 330                 335 gat aaa ttt ggt cgt aag cca ctg caa att atc ggc gca ctc gga atg   1056
Asp Lys Phe Gly Arg Lys Pro Leu Gln Ile Ile Gly Ala Leu Gly Met
            340                 345                 350 gca atc ggt atg ttt agc ctc ggt acc gcg ttt tac act cag gca ccg   1104
Ala Ile Gly Met Phe Ser Leu Gly Thr Ala Phe Tyr Thr Gln Ala Pro
        355                 360                 365 ggt att gtg gca cta ctg tcg atg ctg ttc tat gtt gcc gcc ttt gcc   1152
Gly Ile Val Ala Leu Leu Ser Met Leu Phe Tyr Val Ala Ala Phe Ala
                370                 375                 380 atg tcc tgg ggt ccg gta tgc tgg gta ctg ctg tcg gaa atc ttc ccg   1200
Met Ser Trp Gly Pro Val Cys Trp Val Leu Leu Ser Glu Ile Phe Pro
385                 390                 395                 400 aat gct att cgt ggt aaa gcg ctg gca atc gcg gtg gcg gcc cag tgg   1248
Asn Ala Ile Arg Gly Lys Ala Leu Ala Ile Ala Val Ala Ala Gln Trp
                405                 410                 415 ctg gcg aac tac ttc gtc tcc tgg acc ttc ccg atg atg gac aaa aac   1296
Leu Ala Asn Tyr Phe Val Ser Trp Thr Phe Pro Met Met Asp Lys Asn
```

```
                 Leu Ala Asn Tyr Phe Val Ser Trp Thr Phe Pro Met Met Asp Lys Asn
                                 420                 425                 430 tcc tgg ctg gtg gcc cat ttc cac aac ggt ttc tcc tac tgg att tac              1344
Ser Trp Leu Val Ala His Phe His Asn Gly Phe Ser Tyr Trp Ile Tyr
             435                 440                 445 ggt tgt atg ggc gtt ctg gca gca ctg ttt atg tgg aaa ttt gtc ccg              1392
Gly Cys Met Gly Val Leu Ala Ala Leu Phe Met Trp Lys Phe Val Pro
450                 455                 460 gaa acc aaa ggt aaa acc ctt gag gag ctg gaa gcg ctc tgg gaa ccg              1440
Glu Thr Lys Gly Lys Thr Leu Glu Glu Leu Glu Ala Leu Trp Glu Pro
465                 470                 475                 480 gaa acg aag aaa aca caa caa act gct acg ctg taa                              1476
Glu Thr Lys Lys Thr Gln Gln Thr Ala Thr Leu
                 485                 490

<210> SEQ ID NO 2
<211> LENGTH: 491
<212> TYPE: PRT
<213> ORGANISM: Escherichia coli

<400> SEQUENCE: 2

Met Asn Thr Gln Tyr Asn Ser Ser Tyr Ile Phe Ser Ile Thr Leu Val
1               5                   10                  15

Ala Thr Leu Gly Gly Leu Leu Phe Gly Tyr Asp Thr Ala Val Ile Ser
            20                  25                  30

Gly Thr Val Glu Ser Leu Asn Thr Val Phe Val Ala Pro Gln Asn Leu
        35                  40                  45

Ser Glu Ser Ala Ala Asn Ser Leu Leu Gly Phe Cys Val Ala Ser Ala
    50                  55                  60

Leu Ile Gly Cys Ile Ile Gly Gly Ala Leu Gly Gly Tyr Cys Ser Asn
65                  70                  75                  80

Arg Phe Gly Arg Arg Asp Ser Leu Lys Ile Ala Ala Val Leu Phe Phe
                85                  90                  95

Ile Ser Gly Val Gly Ser Ala Trp Pro Glu Leu Gly Phe Thr Ser Ile
            100                 105                 110

Asn Pro Asp Asn Thr Val Pro Val Tyr Leu Ala Gly Tyr Val Pro Glu
        115                 120                 125

Phe Val Ile Tyr Arg Ile Ile Gly Gly Ile Gly Val Gly Leu Ala Ser
    130                 135                 140

Met Leu Ser Pro Met Tyr Ile Ala Glu Leu Ala Pro Ala His Ile Arg
145                 150                 155                 160

Gly Lys Leu Val Ser Phe Asn Gln Phe Ala Ile Ile Phe Gly Gln Leu
                165                 170                 175

Leu Val Tyr Cys Val Asn Tyr Phe Ile Ala Arg Ser Gly Asp Ala Ser
            180                 185                 190

Trp Leu Asn Thr Asp Gly Trp Arg Tyr Met Phe Ala Ser Glu Cys Ile
        195                 200                 205

Pro Ala Leu Leu Phe Leu Met Leu Leu Tyr Thr Val Pro Glu Ser Pro
    210                 215                 220

Arg Trp Leu Met Ser Arg Gly Lys Gln Glu Gln Ala Glu Gly Ile Leu
225                 230                 235                 240

Arg Lys Ile Met Gly Asn Thr Leu Ala Thr Gln Ala Val Gln Glu Ile
                245                 250                 255

Lys His Ser Leu Asp His Gly Arg Lys Thr Gly Gly Arg Leu Leu Met
            260                 265                 270

Phe Gly Val Gly Val Ile Val Ile Gly Val Met Leu Ser Ile Phe Gln
```

```
                  275                 280                 285
Gln Phe Val Gly Ile Asn Val Val Leu Tyr Tyr Ala Pro Glu Val Phe
290                 295                 300

Lys Thr Leu Gly Ala Ser Thr Asp Ile Ala Leu Leu Gln Thr Ile Ile
305                 310                 315                 320

Val Gly Val Ile Asn Leu Thr Phe Thr Val Leu Ala Ile Met Thr Val
                325                 330                 335

Asp Lys Phe Gly Arg Lys Pro Leu Gln Ile Ile Gly Ala Leu Gly Met
                340                 345                 350

Ala Ile Gly Met Phe Ser Leu Gly Thr Ala Phe Tyr Thr Gln Ala Pro
                355                 360                 365

Gly Ile Val Ala Leu Leu Ser Met Leu Phe Tyr Val Ala Ala Phe Ala
                370                 375                 380

Met Ser Trp Gly Pro Val Cys Trp Val Leu Leu Ser Glu Ile Phe Pro
385                 390                 395                 400

Asn Ala Ile Arg Gly Lys Ala Leu Ala Ile Ala Val Ala Ala Gln Trp
                405                 410                 415

Leu Ala Asn Tyr Phe Val Ser Trp Thr Phe Pro Met Met Asp Lys Asn
                420                 425                 430

Ser Trp Leu Val Ala His Phe His Asn Gly Phe Ser Tyr Trp Ile Tyr
                435                 440                 445

Gly Cys Met Gly Val Leu Ala Ala Leu Phe Met Trp Lys Phe Val Pro
450                 455                 460

Glu Thr Lys Gly Lys Thr Leu Glu Glu Leu Glu Ala Leu Trp Glu Pro
465                 470                 475                 480

Glu Thr Lys Lys Thr Gln Gln Thr Ala Thr Leu
                485                 490

<210> SEQ ID NO 3
<211> LENGTH: 180
<212> TYPE: DNA
<213> ORGANISM: Artificial sequence
<220> FEATURE:
<223> OTHER INFORMATION: hybrid promoter

<400> SEQUENCE: 3
ctagatctct cacctaccaa acaatgcccc cctgcaaaaa ataaattcat aaaaaacata      60
cagataacca tctgcggtga taaattatct ctggcggtgt tgacaattaa tcatcggctc    120
gtataatgtg tggaattgtg agcgtcagaa tggtctaagg caggtctgaa tgaataccca    180

<210> SEQ ID NO 4
<211> LENGTH: 32
<212> TYPE: DNA
<213> ORGANISM: Artificial sequence
<220> FEATURE:
<223> OTHER INFORMATION: primer

<400> SEQUENCE: 4
gtaagatctc tcatgtttga cagcttatca tc                                    32

<210> SEQ ID NO 5
<211> LENGTH: 52
<212> TYPE: DNA
<213> ORGANISM: Artificial sequence
<220> FEATURE:
<223> OTHER INFORMATION: primer

<400> SEQUENCE: 5
```

-continued ggcgctccac ggagcgcctt tttttctttc gtctgcctaa gctttctaga cg        52

<210> SEQ ID NO 6
<211> LENGTH: 55
<212> TYPE: DNA
<213> ORGANISM: Artificial sequence
<220> FEATURE:
<223> OTHER INFORMATION: primer

<400> SEQUENCE: 6
tgggtattca ttcagacctg ccttagacca ttctgacgct cacaattcca cacat     55

<210> SEQ ID NO 7
<211> LENGTH: 19
<212> TYPE: DNA
<213> ORGANISM: Artificial sequence
<220> FEATURE:
<223> OTHER INFORMATION: primer

<400> SEQUENCE: 7
gatcaccatc gtcttcttg                                              19

<210> SEQ ID NO 8
<211> LENGTH: 19
<212> TYPE: DNA
<213> ORGANISM: Artificial sequence
<220> FEATURE:
<223> OTHER INFORMATION: primer

<400> SEQUENCE: 8
gtagcgacta aggtaatcg                                              19

<210> SEQ ID NO 9
<211> LENGTH: 60
<212> TYPE: DNA
<213> ORGANISM: Artificial sequence
<220> FEATURE:
<223> OTHER INFORMATION: primer

<400> SEQUENCE: 9
cacaacacta aacctataag ttggggaaat acaatgtgaa gcctgctttt ttatactaag 60

<210> SEQ ID NO 10
<211> LENGTH: 60
<212> TYPE: DNA
<213> ORGANISM: Artificial sequence
<220> FEATURE:
<223> OTHER INFORMATION: primer

<400> SEQUENCE: 10
gccgatgggc gccatttttc actgcggcaa gaattacgct caagttagta taaaaaagct 60

<210> SEQ ID NO 11
<211> LENGTH: 22
<212> TYPE: DNA
<213> ORGANISM: Artificial sequence
<220> FEATURE:
<223> OTHER INFORMATION: primer

<400> SEQUENCE: 11
tcctggcatt gattcagcct gt                                          22

<210> SEQ ID NO 12
<211> LENGTH: 21
<212> TYPE: DNA
<213> ORGANISM: Artificial sequence

```
<220> FEATURE:
<223> OTHER INFORMATION: primer

<400> SEQUENCE: 12
ccagcagcat gagagcgatg a                                              21

<210> SEQ ID NO 13
<211> LENGTH: 39
<212> TYPE: DNA
<213> ORGANISM: Artificial sequence
<220> FEATURE:
<223> OTHER INFORMATION: primer

<400> SEQUENCE: 13
cccgaattcg gacaggaaga ttacagcgta gcagtttgt                           39

<210> SEQ ID NO 14
<211> LENGTH: 39
<212> TYPE: DNA
<213> ORGANISM: Artificial sequence
<220> FEATURE:
<223> OTHER INFORMATION: primer

<400> SEQUENCE: 14
cccgtcgacg atcagaatgg tctaaggcag gtctgaatg                           39
```

METHOD FOR PRODUCING L-AMINO ACIDS USING BACTERIA OF THE ENTEROBACTERIACEAE FAMILY

This application is a Divisional of, and claims priority under 35 U.S.C. §120 to, U.S. patent application Ser. No. 13/032,057, filed Feb. 22, 2011, which is a Continuation under 35 U.S.C. §120 of U.S. patent application Ser. No. 11/247,138, filed Oct. 12, 2005, now U.S. Pat. No. 7,915,018, which claimed priority under 35 U.S.C. §119 to Russian Application Serial No. 2004/130954, filed Oct. 22, 2004, and U.S. Provisional Patent Application Ser. No. 60/673,807, filed Apr. 22, 2005, the entireties of which are incorporated by reference. Also, the Sequence Listing filed electronically herewith is hereby incorporated by reference (File name: 2012-05-0ST_US-193D_Seq_List; File size: 15 KB; Date recorded: May 8, 2012).

BACKGROUND OF THE INVENTION

1. Technical Field

The present invention relates to a method for producing an L-amino acid by fermentation, and more specifically to genes which aid in this fermentation. These genes are useful for the improvement of L-amino acid production, for example, for production of L-threonine, L-lysine, L-histidine, L-phenylalanine, L-arginine and L-glutamic acid.

2. Background Art

Conventionally, L-amino acids are industrially produced by fermentation methods utilizing strains of microorganisms obtained from natural sources, or mutants thereof. Typically, the microorganisms are modified to enhance production yields of L-amino acids.

Many techniques to enhance production yields of L-amino acids have been reported, including transformation of microorganisms with recombinant DNA (see, for example, U.S. Pat. No. 4,278,765). Other techniques for enhancing production yields include increasing the activities of enzymes involved in amino acid biosynthesis and/or desensitizing the target enzymes to feedback inhibition by the resulting L-amino acid (see, for example, WO 95/16042 or U.S. Pat. Nos. 4,346,170, 5,661,012 and 6,040,160).

Strains useful in production of L-threonine by fermentation are known, including strains with increased activities of enzymes involved in L-threonine biosynthesis (U.S. Pat. Nos. 5,175,107, 5,661,012, 5,705,371, and 5,939,307; EP 0219027), strains resistant to chemicals such as L-threonine and its analogs (WO 01/14525A1, EP 301572 A2, U.S. Pat. No. 5,376,538), strains with target enzymes desensitized to feedback inhibition by the produced L-amino acid or its by-products (U.S. Pat. Nos. 5,175,107 and 5,661,012), and strains with inactivated threonine degradation enzymes (U.S. Pat. Nos. 5,939,307 and 6,297,031).

The known threonine-producing strain VKPM B-3996 (U.S. Pat. Nos. 5,175,107 and 5,705,371) is presently one of the best known threonine producers. For construction of the strain VKPM B-3996, several mutations and a plasmid, described below, were introduced into the parent strain E. coli K-12 (VKPM B-7). Mutant thrA gene (mutation thrA442) encodes aspartokinase homoserine dehydrogenase I, which is resistant to feedback inhibition by threonine. Mutant ilvA gene (mutation ilvA442) encodes threonine deaminase having decreased activity which results in a decreased rate of isoleucine biosynthesis and to a leaky phenotype of isoleucine starvation. In bacteria containing the ilvA442 mutation, transcription of the thrABC operon is not repressed by isoleucine, and therefore is very efficient for threonine production. Inactivation of the tdh gene encoding threonine dehydrogenase results in prevention of threonine degradation. The genetic determinant of saccharose assimilation (scrKYABR genes) was transferred to said strain. To increase expression of the genes controlling threonine biosynthesis, plasmid pVIC40 containing the mutant threonine operon thrA442BC was introduced in the intermediate strain TDH6. The amount of L-threonine accumulated during fermentation of the strain can be up to 85 g/l.

By optimizing the main biosynthetic pathway of a desired compound, further improvement of L-amino acid producing strains can be accomplished via supplementation of the bacterium with increasing amounts of sugars as a carbon source, for example, glucose. Despite the efficiency of glucose transport by PTS, access to the carbon source in a highly productive strain still may be insufficient.

It is known that active transport of sugars and other metabolites into bacterial cells is accomplished by several transport systems. Among these, the XylE protein from E. coli is a D-xylose permease, one of two systems in E. coli responsible for the uptake of D-xylose; the other being the ATP-dependent ABC transporter XylFGH. The cloned xylE gene has been shown to complement xylE mutants in vivo (Davis, E. O. and Henderson, P. J., J. Biol. Chem., 262(29); 13928-32 (1987)). The XylE-mediated transport in whole cells is inhibited by protonophores and elicits an alkaline pH change (Lam, V. M. et al, J. Bacteriol. 143(1); 396-402 (1980)). Experiments using xylE and xylF mutants have established that XylE protein has a $K_M$ of 63-169 µM for D-xylose (Sumiya. M. et al, Receptors Channels, 3(2); 117-28 (1995)). The XylE protein is a member of the major facilitator superfamily (MFS) of transporters (Griffith, J. K. et al, Curr. Opin. Cell Biol. 4(4); 684-95 (1992)) and appears to function as a D-xylose/proton symporter. The xylE gene probably constitutes a monocistronic operon whose expression is inducible by D-xylose. Imported xylose is catabolized to xylulose-5-phosphate by the action of the XylA (xylose isomerase) and XylB (xylulokinase) enzymes. Under appropriate conditions, the xylose isomerase encoded by the xylA gene also efficiently catalyzes the conversion of D-glucose to D-fructose (Wovcha, M. G. et al, Appl Environ Microbiol. 45(4): 1402-4 (1983)).

However, there has been no report to date of using a bacterium of the Enterobacteriaceae family having an enhanced activity of D-xylose permease for increasing the production of L-amino acids.

SUMMARY OF THE INVENTION

Figure 1:
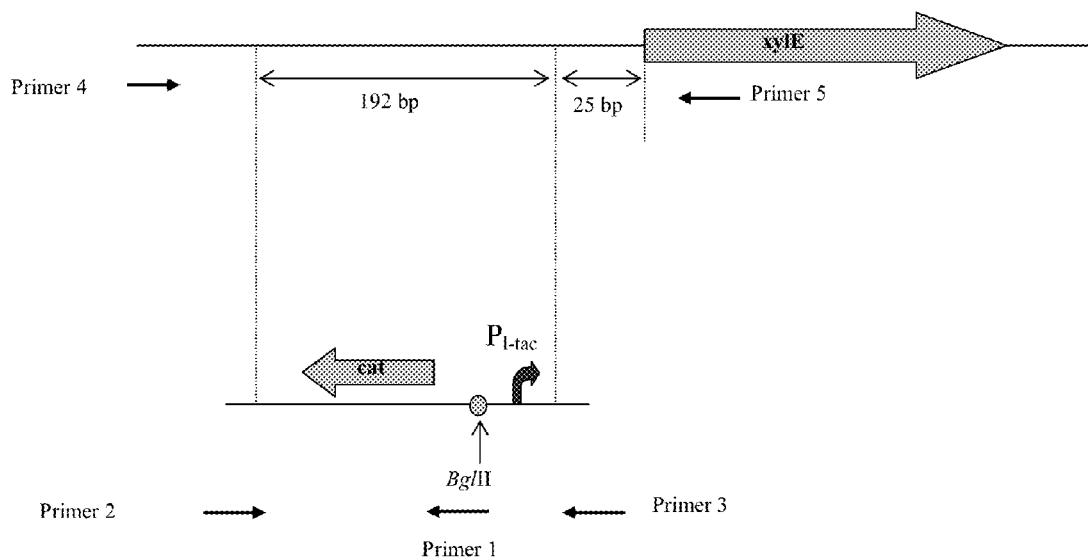
FIG. 1 shows the structure of the region upstream of the xylE gene in the chromosome of E. coli and the structure of an integrated DNA fragment containing the cat gene and a hybrid $P_{L-tac}$ promoter.

An object of present invention is to enhance the productivity of L-amino acid-producing strains and to provide a method for producing non-aromatic or aromatic L-amino acids using these strains.

This aim was achieved by finding that the increasing the expression of the xylE gene encoding D-xylose permease enhances production of L-amino acids, such as L-threonine, L-lysine, L-histidine, L-phenylalanine, L-arginine and L-glutamic acid. Thus the present invention has been completed.

It is an object of the present invention to provide an L-amino acid-producing bacterium of the Enterobacteriaceae family, wherein said bacterium has been modified to enhance an activity of D-xylose permease.

It is a further object of the present invention to provide the bacterium described above, wherein said activity of said D-xylose permease is enhanced by increasing the expression of a gene which encodes D-xylose permease.

It is a further object of the present invention to provide the bacterium described above, wherein said activity of D-xylose permease is enhanced by modifying an expression control sequence of the gene encoding D-xylose permease so that the gene expression is enhanced or by increasing the copy number of the gene encoding D-xylose permease.

It is a further object of the present invention to provide the bacterium described above, wherein said bacterium has been additionally modified to enhance an activity of glucokinase.

It is a further object of the present invention to provide the bacterium described above, wherein said bacterium has been additionally modified to enhance an activity of xylose isomerase.

It is a further object of the present invention to provide the bacterium described above, wherein said bacterium has been modified to increase the expression of the xylABFGHR locus.

It is a further object of the present invention to provide the bacterium described above, wherein the bacterium is selected from the group consisting of the genera *Escherichia, Enterobacter, Erwinia, Klebsiella, Pantoea, Providencia, Salmonella, Serratia, Shigella*, and *Morganella*.

It is a further object of the present invention to provide the bacterium described above, wherein said gene encodes a D-xylose permease selected from the group consisting of:
  (A) a protein which comprises the amino acid sequence of SEQ ID NO: 2; and
  (B) a variant protein of the amino acid sequence shown in SEQ ID NO: 2 which has an activity of D-xylose permease.

It is a further object of the present invention to provide the bacterium described above, wherein said gene encoding D-xylose permease comprises a DNA selected from the group consisting of:
  (a) a DNA which comprises a nucleotide sequence of nucleotides 1 to 1476 in SEQ ID NO: 1; and
  (b) a DNA which is hybridizable with a nucleotide sequence of nucleotides 1-1476 in SEQ ID NO: 1, or a probe which can be prepared from said nucleotide sequence under stringent conditions, and encodes a protein having an activity of D-xylose permease.

It is a further object of the present invention to provide the bacterium described above, wherein said stringent conditions comprise those in which washing is performed at 60° C. at a salt concentration of 1×SSC and 0.1% SDS for 15 minutes.

It is a further object of the present invention to provide the bacterium described above, wherein said bacterium is an L-threonine producing bacterium.

It is a further object of the present invention to provide the bacterium described above, wherein said bacterium has been additionally modified to enhance expression of a gene selected from the group consisting of
  the mutant thrA gene which codes for aspartokinase homoserine dehydrogenase I and is resistant to feedback inhibition by threonine,
  the thrB gene which codes for homoserine kinase,
  the thrC gene which codes for threonine synthase,
  the rhtA gene which codes for a putative transmembrane protein, and
  any combination thereof.

It is a further object of the present invention to provide the bacterium described above, wherein said bacterium has been modified to increase expression of said mutant thrA gene, said thrB gene, said thrC gene, and said rhtA gene.

It is a further object of the present invention to provide the bacterium described above, wherein said bacterium is an L-lysine producing bacterium.

It is a further object of the present invention to provide the bacterium described above, wherein said bacterium is an L-histidine producing bacterium.

It is a further object of the present invention to provide the bacterium described above, wherein said bacterium is an L-phenylalanine producing bacterium.

It is a further object of the present invention to provide the bacterium described above, wherein said bacterium is an L-arginine producing bacterium.

It is a further object of the present invention to provide the bacterium described above, wherein said bacterium is an L-glutamic acid producing bacterium.

It is a further object of the present invention to provide a method for producing an L-amino acid which comprises cultivating the bacterium described above in a culture medium, allowing accumulation of the L-amino acid in the culture medium, and isolating the L-amino acid from the culture medium.

It is a further object of the present invention to provide the method described above, wherein the culture medium contains xylose.

It is a further object of the present invention to provide the method described above, wherein said L-amino acid is L-threonine.

It is a further object of the present invention to provide the method described above, wherein said L-amino acid is L-lysine.

It is a further object of the present invention to provide the method described above, wherein said L-amino acid is L-histidine.

It is a further object of the present invention to provide the method described above, wherein said L-amino acid is L-phenylalanine.

It is a further object of the present invention to provide the method described above, wherein said L-amino acid is L-arginine.

It is a further object of the present invention to provide the method described above, wherein said L-amino acid is L-glutamic acid.

DESCRIPTION OF THE PREFERRED EMBODIMENTS

In the present invention, "L-amino acid-producing bacterium" means a bacterium which has an ability to produce and excrete an L-amino acid in a medium, when the bacterium is cultured in the medium. The L-amino acid-producing ability may be imparted or enhanced by breeding. The term "L-amino acid-producing bacterium" as used herein also means a bacterium which is able to produce and cause accumulation of an L-amino acid in a culture medium in an amount larger than a wild-type or parental strain of *E. coli*, such as *E. coli* K-12, and preferably means that the bacterium is able to cause accumulation in a medium of an amount not less than 0.5 g/L, more preferably not less than 1.0 g/L of the target L-amino acid. The term "L-amino acids" include L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, and L-valine. L-threonine, L-lysine, L-histidine, L-phenylalanine, L-arginine, and L-glutamic acid are particularly preferred.

The Enterobacteriaceae family includes bacteria belonging to the genera *Escherichia, Enterobacter, Erwinia, Klebsiella, Pantoea, Photorhabdus, Providencia, Salmonella, Serratia, Shigella, Morganella, Yersinia*, etc. Specifically, those classified into the Enterobacteriaceae according to the taxonomy used in the NCBI (National Center for Biotechnology Information) database (www.ncbi.nlm.nih.gov/htbin-post/Taxonomy/wgetorg?mode=Tree&id=1236&lvl=3&keep=1&srchmode=1&unlock) can be used. A bacterium belonging to the genus of *Escherichia* or *Pantoea* is preferred.

The phrase "a bacterium belonging to the genus *Escherichia*" means that the bacterium is classified into the genus *Escherichia* according to the classification known to a person skilled in the art of microbiology. Examples of a microorganism belonging to the genus *Escherichia* as used in the present invention include, but are not limited to, *Escherichia coli* (*E. coli*).

The bacterium belonging to the genus *Escherichia* that can be used in the present invention is not particularly limited; however, e.g., bacteria described by Neidhardt, F. C. et al. (*Escherichia coli* and *Salmonella typhimurium*, American Society for Microbiology, Washington D.C., 1208, Table 1) are encompassed by the present invention.

The term "a bacterium belonging to the genus *Pantoea*" means that the bacterium is classified into the genus *Pantoea* according to the classification known to a person skilled in the art of microbiology. Some species of *Enterobacter agglomerans* have been recently re-classified into *Pantoea agglomerans, Pantoea ananatis, Pantoea stewartii* or the like, based on the nucleotide sequence analysis of 16S rRNA etc. (Int. J. Syst. Bacteriol., 43, 162-173 (1993)).

The bacterium of the present invention encompasses a strain of the Enterobacteriaceae family which has an ability to produce an L-amino acid and has been modified to enhance an activity of D-xylose permease. In addition, the bacterium of the present invention encompasses a strain of the Enterobacteriaceae family which has an ability to produce a L-amino acid and does not have a native activity of D-xylose permease, and has been transformed with a DNA fragment encoding D-xylose permease.

The phrase "activity of D-xylose permease" means an activity of transporting sugars, such as xylose and glucose, into the cell. Activity of D-xylose permease can be detected by complementation of growth delay of the bacterium which has a disrupted PTS-system of sugar transport (see, for example, the ΔptsHI-crr mutant described in the Examples) or by complementation xylE mutations in vivo (Davis, E. O. and Henderson, P. J., J. Biol. Chem., 262(29); 13928-32 (1987)).

The phrase "bacterium has been modified to enhance an activity of D-xylose permease" means that the activity per cell is higher than that of a non-modified strain, for example, a wild-type strain. Examples of such modifications include increasing the number of D-xylose permease molecules per cell, increasing the specific activity per D-xylose permease molecule, and so forth. Furthermore, a wild-type strain that may be used for comparison purposes includes, for example, *Escherichia coli* K-12. In the present invention, the amount of the accumulated L-amino acid, for example, L-threonine or L-arginine, can be increased in a culture medium as a result of enhancing the intracellular activity of D-xylose permease.

Enhancement of D-xylose permease activity in a bacterial cell can be attained by increasing the expression of the xylE gene encoding D-xylose permease. Any xylE gene derived from bacteria belonging to the genus *Escherichia*, as well as any xylE gene derived from other bacteria, such as coryneform bacteria, may be used as the D-xylose permease gene in the present invention. The xylE genes derived from bacteria belonging to the genus *Escherichia* are preferred.

The phrase "increasing the expression of the gene" means that the expression amount of the gene is higher than that of a non-modified strain, for example, a wild-type strain. Examples of such modification include increasing the copy number of gene(s) per cell, increasing the expression level of the gene(s), and so forth. The quantity of the copy number of a gene is measured, for example, by restricting the chromosomal DNA followed by Southern blotting using a probe based on the gene sequence, fluorescence in situ hybridization (FISH), and the like. The level of gene expression can be measured by various methods including Northern blotting, quantitative RT-PCR, and the like. Furthermore, a wild-type strain that can act as a control includes, for example, *Escherichia coli* K-12 or *Pantoea ananatis* FERM BP-6614 (US2004180404A1). *Pantoea ananatis* FERM BP-6614 was deposited at the National Institute of Bioscience and Human-Technology, Agency of Industrial Science and Technology, Ministry of International Trade and Industry (currently, International Patent Organism Depositary, National Institute of Advanced Industrial Science and Technology) on Feb. 19, 1998 and received an accession number of FERM P-16644. It was then converted to an international deposit under the provisions of Budapest Treaty on Jan. 11, 1999 and received an accession number of FERM BP-6614. Although this strain was identified as *Enterobacter agglomerans* when it was isolated, it has been re-classified into *Pantoea ananatis* based on nucleotide sequence analysis of 16S rRNA etc. as described above.

As a result of enhancing the intracellular activity of D-xylose permease, L-amino acid accumulation, for example L-threonine, L-lysine, L-histidine, L-phenylalanine or L-glutamic acid accumulation in a medium is increased.

The xylE gene which encodes D-xylose permease, namely D-xylose/proton symporter, from *Escherichia coli* has been elucidated (nucleotide numbers 4240277 to 4238802 in the sequence of GenBank accession NC_000913.2, gi:49175990). The xylE gene is located between the yjbA ORF and the malG gene on the chromosome of *E. coli* K-12. The other xylE genes which encodes D-xylose permease have also been elucidated (AAN45595. xylose-proton sym . . . [gi:24054686], AAM41050. MFS transporter . . . [gi: 21112853]: *Xanthomonas campestris*: XCC1759). In the present invention, the xylE gene from *Escherichia coli* is represented by SEQ ID NO. 1.

Upon being transported into the cell, glucose is phosphorylated by glucokinase, which is encoded by the glk gene. So, it is also desirable to modify the bacterium to have enhanced activity of glucokinase. The glk gene which encodes glucokinase of *Escherichia coli* has been elucidated (nucleotide numbers 2506481 to 2507446 in the sequence of GenBank accession NC_000913.1, gi:16127994). The glk gene is located between the b2387 and the b2389 ORFs on the chromosome of *E. coli* K-12.

Under appropriate conditions, the xylose isomerase encoded by the xylA gene also efficiently catalyzes the conversion of D-glucose to D-fructose (Wovcha, M. G. et al, Appl Environ Microbiol. 45(4): 1402-4 (1983)). So, it is also desirable to modify the bacterium to have an enhanced activity of xylose isomerase. The xylA gene which encodes xylose isomerase of *Escherichia coli* has been elucidated (nucleotide numbers 3728788 to 3727466 in the sequence of GenBank accession NC_000913.2, gi: 49175990). The xylA gene is located between the xylB and xylF genes on the chromosome of *E. coli* K-12.

When the culture medium contains xylose as an additional carbon source, increasing the activity of the xylose utilization enzymes is necessary. The "xylose utilization enzymes" include enzymes of xylose transport, xylose isomerization and xylose phosphorylation, and regulatory proteins. Such enzymes include xylose isomerase, xylulokinase, xylose transporters, and xylose transcriptional activator. Xylose isomerase catalyzes the reaction of isomerization of D-xylose to D-xylulose. Xylulokinase catalyzes the reaction of phosphorylation of D-xylulose using ATP yielding D-xylulose-5-phosphate and ADP. The presence of activity of xylose utilization enzymes, such as xylose isomerase and xylulokinase, is determined by complementation of corresponding xylose isomerase-negative or xylulokinase-negative *E. coli* mutants, respectively.

Genes coding for the above mentioned xylose utilization enzymes are located in the xylABFGHR locus on the chromosome of *Escherichia coli*. The gene coding for xylulokinase (EC numbers 2.7.1.17) is known and has been designated xylB (nucleotide numbers 3725546 to 3727000 in the sequence of GenBank accession NC_000913.1, gi:16131435). The gene coding for the xylose binding protein transport system is known and has been designated xylF (nucleotide numbers 3728760 to 3729752 in the sequence of GenBank accession NC_000913.1, gi:16131437). The gene coding for the putative ATP-binding protein of the xylose transport system is known and has been designated xylG (nucleotide numbers 3729830 to 3731371 in the sequence of GenBank accession NC_000913.1, gi:16131438). The gene coding for the permease component of the ABC-type xylose transport system is known and has been designated xylH (nucleotide numbers 3731349 to 3732530 in the sequence of GenBank accession NC_000913.1, gi:16131439). The gene coding for the transcriptional regulator of the xyl operon is known and has been designated xylR (nucleotide numbers 3732608 to 3733786 in the sequence of GenBank accession NC_000913.1, gi:16131440).

Therefore, xylE, glk and genes of the xylABFGHR locus can be obtained by PCR (polymerase chain reaction; refer to White, T. J. et al., *Trends Genet.*, 5, 185 (1989)) utilizing primers prepared based on the known nucleotide sequence of the gene. Genes coding for D-xylose permease of other microorganisms can be obtained in a similar manner.

The xylE gene derived from *Escherichia coli* is exemplified by a DNA which encodes the following protein (A) or (B):

(A) a protein which has the amino acid sequence shown in SEQ ID NO: 2; or (B) a variant protein of the amino acid sequence shown in SEQ ID NO: 2, which has an activity of D-xylose permease.

The phrase "variant protein" as used in the present invention means a protein which has changes in the sequence, whether they are deletions, insertions, additions, or substitutions of amino acids, but still maintains the desired activity at a useful level, for example, useful for the enhanced production of an L-amino acid. The number of changes in the variant protein depends on the position or the type of amino acid residues in the three dimensional structure of the protein. It may be 2 to 30, preferably 2 to 15, and more preferably 2 to 5 for the protein (A). These changes in the variants can occur in regions of the protein which are not critical for the function of the protein. This is because some amino acids have high homology to one another so the three dimensional structure or activity is not affected by such a change. These changes in the variant protein can occur in regions of the protein which are not critical for the function of the protein. Therefore, the protein variant (B) may be one which has a homology of not less than 70%, preferably 80%, and more preferably 90%, and most preferably 95% with respect to the entire amino acid sequence of D-xylose permease shown in SEQ ID NO. 2, as long as the activity of D-xylose permease is maintained. Homology between two amino acid sequences can be determined using the well-known methods, for example, the computer program BLAST 2.0, which calculates three parameters: score, identity and similarity.

The DNA, which encodes substantially the same protein as the D-xylose permease described above, may be obtained, for example, by modifying the nucleotide sequence of DNA encoding D-xylose permease (SEQ ID NO: 1), for example, by means of the site-directed mutagenesis method so that one or more amino acid residues at a specified site involve deletion, substitution, insertion, or addition. A DNA modified as described above may be obtained by conventionally known mutation treatments. Such treatments include hydroxylamine treatment of the DNA encoding proteins of the present invention, or treatment of the bacterium containing the DNA with UV irradiation or a reagent such as N-methyl-N'-nitro-N-nitrosoguanidine or nitrous acid.

The substitution, deletion, insertion or addition of one or several amino acid residues should be conservative mutation(s) so that the activity is maintained. The representative conservative mutation is a conservative substitution. Examples of conservative substitutions include substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Be, substitution of Be, Met, Val or Phe for Leu, substitution of Asn, Glu, Gln, His or Arg for Lys, substitution of Be, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Be or Leu for Val.

A DNA encoding substantially the same protein as D-xylose permease can be obtained by expressing a DNA having the mutation as described above in an appropriate cell, and investigating the activity of any expressed product. A DNA encoding substantially the same protein as D-xylose permease can also be obtained by isolating a DNA, that is hybridizable with a probe having a nucleotide sequence which contains, for example, the nucleotide sequence shown as SEQ ID NO: 1, under the stringent conditions, and encodes a protein having the D-xylose permease activity. The "stringent conditions" referred to herein are conditions under which so-called specific hybrids are formed, and non-specific hybrids are not formed. For example, stringent conditions can be exemplified by conditions under which DNAs having high homology, for example, DNAs having homology of not less than 50%, preferably 80%, and still more preferably 90%, and most preferably 95% are able to hybridize with each other, but DNAs having homology lower than the above are not able to hybridize with each other. Alternatively, stringent conditions may be exemplified by conditions under which DNA is able to hybridize at a salt concentration equivalent to ordinary washing conditions in Southern hybridization, i.e., 1×SSC, 0.1% SDS, preferably 0.1×SSC, 0.1% SDS, at 60° C. Duration of washing depends on the type of membrane used for blotting and, as a rule, what is recommended by the manufacturer. For example, recommended duration of washing the Hybond™ N+ nylon membrane (Amersham) under stringent conditions is 15 minutes. Preferably, washing may be performed 2 to 3 times.

A partial sequence of the nucleotide sequence of SEQ ID NO: 1 can also be used as a probe. Probes may be prepared by PCR using primers based on the nucleotide sequence of SEQ ID NO: 1, and a DNA fragment containing the nucleotide sequence of SEQ ID NO: 1 as a template. When a DNA fragment having a length of about 300 bp is used as the probe, the hybridization conditions for washing include, for example, 50° C., 2×SSC and 0.1% SDS.

The substitution, deletion, insertion, or addition of nucleotides as described above also includes mutation which naturally occurs (mutant or variant), for example, due to variety in the species or genus of bacteria, and which contains the D-xylose permease.

"Transformation of a bacterium with DNA encoding a protein" means introduction of the DNA into a bacterium, for example, by conventional methods. Transformation of this DNA will result in an increase in expression of the gene encoding the protein of the present invention, and will enhance the activity of the protein in the bacterial cell. Methods of transformation include any known methods that have hitherto been reported. For example, a method of treating recipient cells with calcium chloride so as to increase permeability of the cells to DNA has been reported for *Escherichia coli* K-12 (Mandel, M. and Higa, A., *J. Mol. Biol.*, 53, 159 (1970)) and may be used.

Methods of gene expression enhancement include increasing the gene copy number. Introducing a gene into a vector that is able to function in a bacterium of the Enterobacteriaceae family increases the copy number of the gene. Preferably, low copy vectors are used. Examples of low-copy vectors include, but are not limited to, pSC101, pMW118, pMW119, and the like. The term "low copy vector" is used for vectors, the copy number of which is up to 5 copies per cell.

Enhancement of gene expression may also be achieved by introduction of multiple copies of the gene into a bacterial chromosome by, for example, a method of homologous recombination, Mu integration or the like. For example, one act of Mu integration allows introduction of up to 3 copies of the gene into a bacterial chromosome.

Increasing the copy number of the D-xylose permease gene can also be achieved by introducing multiple copies of the D-xylose permease gene into the chromosomal DNA of the bacterium. In order to introduce multiple copies of the gene into a bacterial chromosome, homologous recombination is carried out using a sequence whose multiple copies exist as targets in the chromosomal DNA. Sequences having multiple copies in the chromosomal DNA include, but are not limited to, repetitive DNA, or inverted repeats existing at the end of a transposable element. Also, as disclosed in U.S. Pat. No. 5,595,889, it is possible to incorporate the D-xylose permease gene into a transposon, and allow it to be transferred to introduce multiple copies of the gene into the chromosomal DNA.

Enhancement of gene expression may also be achieved by placing the DNA of the present invention under the control of a potent promoter. For example, the lac promoter, the trp promoter, the trc promoter, and the $P_R$ or the $P_L$ promoter of lambda phage are known as potent promoters. Enhancement of gene expression may also be achieved by placing a potent terminator downstream of the DNA of the present invention. Use of a potent promoter and/or terminator can be combined with multiplication of gene copies. Alternatively, the effect of a promoter can be enhanced by, for example, introducing a mutation into the promoter to increase the transcription level of a structural gene (coding region of a gene) located downstream of the promoter. Similarly, the effect of a terminator can be enhanced by, for example, introducing a mutation into the terminator to increase the turnover of transcription of a gene located upstream of the terminator.

Furthermore, it is known that substitution of several nucleotides in the spacer between ribosome binding site (RBS) and the start codon, especially the sequences immediately upstream of the start codon, profoundly affect the mRNA translatability. For example, a 20-fold range in the expression levels was found, depending on the nature of the three nucleotides preceding the start codon (Gold et al., Annu. Rev. Microbiol., 35, 365-403, 1981; Hui et al., EMBO J., 3, 623-629, 1984). Previously, it was shown that the rhtA23 mutation is an A-for-G substitution at the −1 position relative to the ATG start codon (ABSTRACTS of $17^{th}$ International Congress of Biochemistry and Molecular Biology in conjugation with 1997 Annual Meeting of the American Society for Biochemistry and Molecular Biology, San Francisco, Calif. Aug. 24-29, 1997, abstract No. 457). Therefore, it may be suggested that the rhtA23 mutation enhances the rhtA gene expression and, as a consequence, increases the resistance to threonine, homoserine and some other substances transported out of cells.

Moreover, it is also possible to introduce a nucleotide substitution into a promoter or terminator region of the D-xylose permease gene on the bacterial chromosome, which results in a stronger promoter or terminator function. The alteration of the expression control sequence can be performed, for example, in the same manner as the gene substitution using a temperature-sensitive plasmid, as disclosed in International Patent Publication WO 00/18935 and Japanese Patent Application Laid-Open No. 1-215280.

Methods for preparation of plasmid DNA include, but are not limited to, digestion and ligation of DNA, transformation, selection of an oligonucleotide as a primer and the like, or other methods well known to one skilled in the art. These methods are described, for instance, in Sambrook, J., Fritsch, E. F., and Maniatis, T., "Molecular Cloning A Laboratory Manual, Second Edition", Cold Spring Harbor Laboratory Press (1989).

The bacterium of the present invention can be obtained by introduction of the aforementioned DNAs into a bacterium which inherently has the ability to produce an L-amino acid. Alternatively, the bacterium of the present invention can be obtained by imparting an ability to produce an L-amino acid to a bacterium already containing the DNAs.

L-Threonine Producing Bacteria

Examples of parent strains for deriving the L-threonine-producing bacteria of the present invention include, but are not limited to, L-threonine-producing bacteria belonging to the genus *Escherichia*, such as *E. coli* TDH-6/pVIC40 (VKPM B-3996) (U.S. Pat. Nos. 5,175,107 and 5,705,371), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 1978, 14: 947-956), *E. coli* VL643 and VL2055 (EP 1149911 A), and the like.

The strain TDH-6 is deficient in the thrC gene, as well as being sucrose-assimilative, and the ilvA gene has a leaky mutation. This strain also has a mutation in the rhtA gene, which imparts resistance to high concentrations of threonine or homoserine. The strain B-3996 contains the plasmid pVIC40 which was obtained by inserting a thrA*BC operon which includes a mutant thrA gene into a RSF1010-derived vector. This mutant thrA gene encodes aspartokinase homoserine dehydrogenase I which has substantially desensitized feedback inhibition by threonine. The strain B-3996 was deposited in the All-Union Scientific Center of Antibiotics (Nagatinskaya Street 3-A, 117105 Moscow, Russian Federation) on Nov. 19, 1987 under accession number RIA 1867. The strain was also deposited in the Russian National Collection of Industrial Microorganisms (VKPM; Dorozhny proezd. 1, Moscow 117545, Russian Federation) under accession number B-3996.

Preferably, the bacterium of the present invention is additionally modified to enhance expression of one or more of the following genes:

the mutant thrA gene which encodes aspartokinase homoserine dehydrogenase I resistant to feedback inhibition by threonine;
the thrB gene which encodes homoserine kinase;
the thrC gene which encodes threonine synthase;
the rhtA gene which encodes a putative transmembrane protein;
the asd gene which encodes aspartate-β-semialdehyde dehydrogenase; and
the aspC gene which encodes aspartate aminotransferase (aspartate transaminase);

The thrA gene which encodes aspartokinase homoserine dehydrogenase I of *Escherichia coli* has been elucidated (nucleotide positions 337 to 2799, GenBank accession no. NC_000913.2, gi: 49175990). The thrA gene is located between the thrL and thrB genes on the chromosome of *E. coli* K-12. The thrB gene which encodes homoserine kinase of *Escherichia coli* has been elucidated (nucleotide positions 2801 to 3733, GenBank accession no. NC_000913.2, gi: 49175990). The thrB gene is located between thrA and thrC genes on the chromosome of *E. coli* K-12. The thrC gene which encodes threonine synthase of *Escherichia coli* has been elucidated (nucleotide positions 3734 to 5020, GenBank accession no. NC_000913.2, gi: 49175990). The thrC gene is located between the thrB gene and the yaaX open reading frame on the chromosome of *E. coli* K-12. All three genes function as a single threonine operon.

A mutant thrA gene which encodes aspartokinase homoserine dehydrogenase I resistant to feedback inhibition by threonine, as well as the thrB and thrC genes, can be obtained as one operon from the well-known plasmid pVIC40 which is present in the threonine producing *E. coli* VKPM B-3996. Plasmid pVIC40 is described in detail in U.S. Pat. No. 5,705,371.

The rhtA gene exists at 18 min on the *E. coli* chromosome close to the glnHPQ operon, which encodes components of the glutamine transport system. The rhtA gene is identical to ORF1 (ybiF gene, positions 764 to 1651, GenBank accession no. AAA218541, gi:440181) and located between the pexB and ompX genes. The unit expressing a protein encoded by the ORF1 has been designated the rhtA gene (rht: resistance to homoserine and threonine). Also, it was revealed that the rhtA23 mutation is an A-for-G substitution at position −1 with respect to the ATG start codon (ABSTRACTS of the 17$^{th}$ International Congress of Biochemistry and Molecular Biology in conjugation with the Annual Meeting of the American Society for Biochemistry and Molecular Biology, San Francisco, Calif., Aug. 24-29, 1997, abstract No. 457, EP 1013765 A).

The asd gene of *E. coli* has already been elucidated (nucleotide positions 3572511 to 3571408, GenBank accession no. NC_000913.1, gi:16131307), and can be obtained by PCR (polymerase chain reaction; refer to White, T. J. et al., Trends Genet., 1989, 5:185), utilizing primers based on the nucleotide sequence of the gene. The asd genes of other microorganisms can be obtained in a similar manner.

Also, the aspC gene of *E. coli* has already been elucidated (nucleotide positions 983742 to 984932, GenBank accession no. NC_000913.1, gi:16128895), and can be obtained by PCR. The aspC genes of other microorganisms can be obtained in a similar manner.

L-Lysine Producing Bacteria

Examples of L-lysine producing bacteria belonging to the genus *Escherichia* include mutants having resistance to an L-lysine analogue. The L-lysine analogue inhibits growth of bacteria belonging to the genus *Escherichia*, but this inhibition is fully or partially desensitized when L-lysine coexists in a medium. Examples of the L-lysine analogue include, but are not limited to, oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting bacteria belonging to the genus *Escherichia* to a conventional artificial mutagenesis treatment. Specific examples of bacterial strains useful for producing L-lysine include *Escherichia coli* AJ11442 (FERM BP-1543, NRRL B-12185; see U.S. Pat. No. 4,346,170) and *Escherichia coli* VL611. In these microorganisms, feedback inhibition of aspartokinase by L-lysine is desensitized.

The strain WC196 may be used as an L-lysine producing bacterium of *Escherichia coli*. This bacterial strain was bred by conferring AEC resistance to the strain W3110, which was derived from *Escherichia coli* K-12. The resulting strain was designated as the *Escherichia coli* AJ13069 strain, and was deposited at the National Institute of Bioscience and Human-Technology, Agency of Industrial Science and Technology (currently National Institute of Advanced Industrial Science and Technology, International Patent Organism Depositary, Tsukuba Central 6, 1-1, Higashi 1-Chome, Tsukuba-shi, Ibaraki-ken, 305-8566, Japan) on Dec. 6, 1994 and received an accession number of FERM P-14690. Then, it was converted to an international deposit under the provisions of the Budapest Treaty on Sep. 29, 1995, and received an accession number of FERM BP-5252 (U.S. Pat. No. 5,827,698).

L-Histidine Producing Bacteria

Examples of parent strains for deriving the L-histidine-producing bacteria of the present invention include, but are not limited to, L-histidine-producing bacteria belonging to the genus *Escherichia*, such as *E. coli* strain 24 (VKPM B-5945, RU2003677); *E. coli* strain 80 (VKPM B-7270, RU2119536); *E. coli* NRRL B-12116-B12121 (U.S. Pat. No. 4,388,405); *E. coli* H-9342 (FERM BP-6675) and H-9343 (FERM BP-6676) (U.S. Pat. No. 6,344,347); *E. coli* H-9341 (FERM BP-6674) (EP 1085087); *E. coli* AI80/pFM201 (U.S. Pat. No. 6,258,554), and the like.

L-Phenylalanine Producing Bacteria

Examples of parent strains for deriving the L-phenylalanine-producing bacteria of the present invention include, but are not limited to, L-phenylalanine-producing bacteria belonging to the genus *Escherichia*, such as *E. coli* AJ12739 (tyrA::Tn10, tyrR) (VKPM B-8197); *E. coli* HW1089 (ATCC 55371) harboring the pheA34 gene (U.S. Pat. No. 5,354,672); *E. coli* MWEC101-b (KR8903681); *E. coli* NRRL B-12141, NRRL B-12145, NRRL B-12146, and NRRL B-12147 (U.S. Pat. No. 4,407,952). Also, as a parent strain, *E. coli* K-12 [W3110 (tyrA)/pPHAB (FERM BP-3566), *E. coli* K-12

[W3110 (tyrA)/pPHAD] (FERM BP-12659), *E. coli* K-12 [W3110 (tyrA)/pPHATerm] (FERM BP-12662), and *E. coli* K-12 [W3110 (tyrA)/pBR-aroG4, pACMAB] named AJ 12604 (FERM BP-3579) may be used (EP 488424 B1). Furthermore, L-phenylalanine-producing bacteria belonging to the genus *Escherichia* with an enhanced activity of the protein encoded by the yedA gene or the yddG gene may also be used (U.S. Patent Applications 2003/0148473 A1 and 2003/0157667 A1).

L-Arginine Producing Bacteria

Examples of parent strains for deriving the L-arginine-producing bacteria of the present invention include, but are not limited to, L-arginine-producing bacteria, such as *E. coli* strain 237 (VKPM B-7925) (U.S. Patent Application 2002/0058315 A1) and its derivative strains harboring mutant N-acetylglutamate synthase (Russian Patent Application No. 2001112869), *E. coli* strain 382 (VKPM B-7926) (EP 1170358 A1), an arginine-producing strain which has the argA gene encoding N-acetylglutamate synthetase introduced therein (JP 57-5693A), and the like.

L-Glutamic Acid Producing Bacteria

Examples of parent strains for deriving the L-glutamic acid-producing bacteria of the present invention include, but are not limited to, L-glutamic acid-producing bacteria belonging to the genus *Escherichia*, such as *E. coli* VL334thrC$^+$ (EP 1172433). *E. coli* VL334 (VKPM B-1641) is an L-isoleucine and L-threonine auxotrophic strain having mutations in the thrC and ilvA genes (U.S. Pat. No. 4,278,765). A wild-type allele of the thrC gene was transferred by the method of general transduction, using bacteriophage P1 grown on wild-type *E. coli* K12 (VKPM B-7) cells. As a result, an L-isoleucine auxotrophic strain VL334thrC$^+$ (VKPM B-8961) was obtained. This strain is able to produce L-glutamic acid.

Examples of parent strains for deriving the L-glutamic acid-producing bacteria of the present invention include, but are not limited to, mutants which are deficient in α-ketoglutarate dehydrogenase activity or mutants which have a reduced α-ketoglutarate dehydrogenase activity. Bacteria belonging to the genus *Escherichia* deficient in α-ketoglutarate dehydrogenase activity or having a reduced α-ketoglutarate dehydrogenase activity and methods for obtaining them are described in U.S. Pat. Nos. 5,378,616 and 5,573,945. Specifically, these strains include the following:

*E. coli* W3110sucA::Kmr
*E. coli* AJ12624 (FERM BP-3853)
*E. coli* AJ12628 (FERM BP-3854)
*E. coli* AJ12949 (FERM BP-4881)

*E. coli* W3110sucA::Kmr is obtained by disrupting the α-ketoglutarate dehydrogenase gene (hereinafter referred to as "sucA gene") of *E. coli* W3110. This strain is completely deficient in α-ketoglutarate dehydrogenase.

Other examples of L-glutamic acid-producing bacteria include mutant strains belonging to the genus *Pantoea* which are deficient in α-ketoglutarate dehydrogenase activity or have a decreased α-ketoglutarate dehydrogenase activity, and can be obtained as described above. Such strains include *Pantoea ananatis* AJ13356. (U.S. Pat. No. 6,331,419). *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Feb. 19, 1998 under accession no. FERM P-16645. It was then converted to an international deposit under the provisions of the Budapest Treaty on Jan. 11, 1999 and received accession no. FERM BP-6615. *Pantoea ananatis* AJ13356 is deficient in α-ketoglutarate dehydrogenase activity as a result of disruption of the aKGDH-E1 subunit gene (sucA). The above strain was identified as *Enterobacter agglomerans* when it was isolated and deposited as *Enterobacter agglomerans* AJ13356. However, it was recently re-classified as *Pantoea ananatis* on the basis of nucleotide sequencing of 16S rRNA and so forth. Although AJ13356 was deposited at the aforementioned depository as *Enterobacter agglomerans*, for the purposes of this specification, they are described as *Pantoea ananatis*.

Production of L-Amino Acids

Oxaloacetate (OAA) serves as a substrate for the reaction which results in synthesis of Thr and Lys. OAA results from a reaction of PEP with phosphoenol pyrvate carboxlase (PEPC) functioning as a catalyst. Therefore, elevation of the PEPC concentration in a cell can be very important for fermentative production of these amino acids. When using glucose as the carbon source in fermentation, glucose is internalized by the glucose-phosphontransferase (Glc-PTS) system. This system consumes PEP, and proteins in the PTS are encoded by ptsG and ptsHIcrr. During internalization, one molecule of PEP and one molecule of pyruvate (Pyr) are generated from one molecule of glucose.

An L-threonine-producing strain and an L-lysine-producing strain which have been modified to have an ability to utilize sucrose (Scr-PTS) have higher productivity of these amino acids when cultured in sucrose rather than glucose (EP 1149911 A2). It is believed that three molecules of PEP and one molecule of Pyr are generated from one molecule of sucrose by the Scr-PTS, increasing the ratio of PEP/Pyr, and thereby facilitating the synthesis of Thr and Lys from sucrose. Furthermore, it has been reported that Glc-PTS is subject to several expression controls (Postma P. W. et al., Microbiol Rev., 57(3), 543-94 (1993); Clark B. et al. J. Gen. Microbiol., 96(2), 191-201 (1976); Plumbridge J., Curr. Opin. Microbiol., 5(2), 187-93 (2002); Ryu S. et al., J. Biol. Chem., 270(6):2489-96 (1995)), and hence it is possible that the incorporation of glucose itself can be a rate-limiting step in amino acid fermentation.

Increasing the ratio of PEP/Pyr even more by increasing expression of the xylE gene in a threonine-producing strain, a lysine-producing strain, a histidine-producing strain, a phenylalanine-producing strain and/or a glutamic acid-producing strain should further increase amino acid production. Because four molecules of PEP are generated from two molecules of glucose, the ratio of PEP/Pyr is expected to be greatly improved. Due to the increased expression of the xylE gene, removal of the expression control of glc-PTS is expected.

The method for producing an L-amino acid of the present invention includes the steps of cultivating the bacterium of the present invention in a culture medium, allowing the L-amino acid to accumulate in the culture medium, and collecting the L-amino acid from the culture medium. Furthermore, the method of the present invention includes a method for producing L-threonine, L-lysine, L-histidine, L-phenylalanine, L-arginine or L-glutamic acid, including the steps of cultivating the bacterium of the present invention in a culture medium, allowing L-threonine, L-lysine, L-histidine, L-phenylalanine, L-arginine or L-glutamic acid to accumulate in the culture medium, and collecting L-threonine, L-lysine, L-histidine, L-phenylalanine, L-arginine or L-glutamic acid from the culture medium.

In the present invention, the cultivation, collection and purification of L-amino acids from the medium and the like may be performed by conventional fermentation methods wherein an L-amino acid is produced using a microorganism.

The culture medium may be either synthetic or natural, so long as the medium includes a carbon source and a nitrogen source and minerals, and if necessary, appropriate amounts of nutrients which the microorganism requires for growth. The carbon source may include various carbohydrates such as glucose, sucrose and xylose, and various organic acids. Depending on the mode of assimilation of the chosen microorganism, alcohols including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganism may be used. As minerals, potassium monophosphate, magnesium sulfate, sodium chloride, ferrous sulfate, manganese sulfate, calcium chloride, and the like may be used. As vitamins, thiamine, yeast extract, and the like may be used. Additional nutrients may be added to the medium, if necessary. For example, if the microorganism requires an L-amino acid for growth (L-amino acid auxotrophy), a sufficient amount of the L-amino acid may be added to the cultivation medium.

The cultivation is performed preferably under aerobic conditions such as a shaking culture, and stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to accumulation of the target L-amino acid in the liquid medium.

After cultivation, solids such as cells can be removed from the liquid medium by centrifugation or membrane filtration, and then the target L-amino acid can be collected and purified by ion-exchange, concentration and/or crystallization methods.

EXAMPLES

The present invention will be more concretely explained below with reference to the following non-limiting examples.

Example 1

Substitution of the Native Promoter Region of the xylE Gene in *E. Coli* by Hybrid $P_{L\text{-}tac}$ Promoter To substitute the native promoter region of the xylE gene, a DNA fragment carrying a hybrid $P_{L\text{-}tac}$ promoter and chloramphenicol resistance marker ($Cm^R$) encoded by the cat gene was integrated into the chromosome of the *E. coli* MG1655 (ATCC 700926) in place of the native promoter region by the method described by Datsenko K. A. and Wanner B. L. (Proc. Natl. Acad. Sci. USA, 2000, 97, 6640-6645) which is also called as a "Red-mediated integration" and/or "Red-driven integration". The recombinant plasmid pKD46 (Datsenko, K. A., Wanner, B. L., Proc. Natl. Acad. Sci. USA, 2000, 97, 6640-6645) having a thermosensitive replicon was used as the donor of the phage λ-derived genes responsible for the Red-mediated recombination system. *Escherichia coli* strain BW25113 containing the recombinant plasmid pKD46 can be obtained from the *E. coli* Genetic Stock Center, Yale University, New Haven, USA, the accession number of which is CGSC7630.

The hybrid $P_{L\text{-}tac}$ promoter was synthesized chemically. The nucleotide sequence of the substituted promoter is presented in the Sequence listing (SEQ ID NO: 3). The synthesized DNA fragment containing the hybrid $P_{L\text{-}tac}$ promoter contains a BglII recognition site at the 5'-end thereof, which is necessary for further joining to the cat gene and 36 nucleotides homologous to the 5'-terminus of the xylE gene introduced for further integration into the bacterial chromosome.

A DNA fragment containing a $Cm^R$ marker encoded by the cat gene was obtained by PCR using the commercially available plasmid pACYC184 (GenBank/EMBL accession number X06403, "Fermentas", Lithuania) as the template, and primers P1 (SEQ ID NO: 4) and P2 (SEQ ID NO: 5). Primer P1 contains a BglII recognition site at the 5'-end thereof, which is necessary for further joining to the hybrid $P_{L\text{-}tac}$ promoter and primer P2 contains 36 nucleotides homologous to the region located 217 bp upstream of the start codon of the xylE gene, which was introduced into the primer for further integration into the bacterial chromosome.

PCR was provided using the "TermoHybaid PCR Express" amplificator. The reaction mixture (total volume—50 µl) consisted of 5 µl of 10×PCR-buffer with 15 mM $MgCl_2$ ("Fermentas", Lithuania), 200 µM each of dNTP, 25 µmol each of the exploited primers and 1 U of Taq-polymerase ("Fermentas", Lithuania). Approximately 5 ng of the plasmid DNA was added into the reaction mixture as a template DNA for the PCR amplification. The temperature profile was the following: initial DNA denaturation for 5 min at 95° C., followed by 25 cycles of denaturation at 95° C. for 30 sec, annealing at 55° C. for 30 sec, elongation at 72° C. for 30 sec; and the final elongation for 7 min at +72° C. Then, the amplified DNA fragment was purified by agarose gel-electrophoresis, extracted using "GenElute Spin Columns" ("Sigma", USA) and precipitated by ethanol.

Each of the two above-described DNA fragments was treated with BglII restrictase and ligated. The ligation product was amplified by PCR using primers P2 (SEQ ID NO: 5) and P3 (SEQ ID NO: 6). Primer P3 contains 36 nucleotides at 5'-end thereof which are homologous to the 5'-terminus of the xylE gene introduced for further integration into the bacterial chromosome.

The amplified DNA fragment was purified by agarose gel-electrophoresis, extracted using "GenElute Spin Columns" ("Sigma", USA) and precipitated by ethanol. The obtained DNA fragment was used for electroporation and Red-mediated integration into the bacterial chromosome of the *E. coli* MG1655/pKD46.

MG1655/pKD46 cells were grown overnight at 30° C. in the liquid LB-medium with the addition of ampicillin (100 µg/ml), then diluted 1:100 with the SOB-medium (Yeast extract, 5 g/l; NaCl, 0.5 g/l; Tryptone, 20 g/l; KCl, 2.5 mM; $MgCl_2$, 10 mM) with the addition of ampicillin (100 µg/ml) and L-arabinose (10 mM) (arabinose is used for inducing the plasmid encoding genes of the Red system) and grown at 30° C. to reach the optical density of the bacterial culture $OD_{600}$=0.4-0.7. Grown cells from 10 ml of the bacterial culture were washed 3 times with the ice-cold de-ionized water, followed by suspending in 100 µl of the water. 10 µl of DNA fragment (100 ng) dissolved in the de-ionized water was added to the cell suspension. The electroporation was performed by "Bio-Rad" electroporator (USA) (No. 165-2098, version 2-89) according to the manufacturer's instructions. Shocked cells were added to 1-ml of SOC medium (Sambrook et al, "Molecular Cloning A Laboratory Manual, Second Edition", Cold Spring Harbor Laboratory Press (1989)), incubated 2 hours at 37° C., and then were spread onto L-agar containing 25 µg/ml of chloramphenicol. Colonies grown within 24 hours were tested for the presence of $Cm^R$ marker, instead of the native promoter region of the xylE gene by PCR using primers P4 (SEQ ID NO: 7) and P5 (SEQ ID NO: 8). For this purpose, a freshly isolated colony was suspended in 20 μl water and then 1 μl of obtained suspension was used for PCR. The following temperature profile was used: initial DNA denaturation for 10 min at 95° C.; then 30 cycles of denaturation at 95° C. for 30 sec, annealing at 55° C. for 30 sec and elongation at 72° C. for 1 min; the final elongation for 7 min at 72° C. A few $Cm^R$ colonies tested contained the desired ~2000 bp DNA fragment, confirming the presence of $Cm^R$ marker DNA instead of 192 bp native promoter region of xylE gene (see FIG. 1). One of these strains was cured from the thermosensitive plasmid pKD46 by culturing at 37° C. and the resulting strain was named as *E. coli* MG1655$P_{L-tac}$xylE.

Example 2

Effect of Increasing the xylE Gene Expression on Growth of an *E. Coli* Strain Having a Disrupted PTS Transport System To show the effect of enhanced expression of the xylE gene on growth of an *E. coli* strain, the *E. coli* strain having a disrupted PTS transport system was constructed.

For that purpose, the DNA fragment carrying kanamycin resistance marker ($Km^R$) was integrated into the chromosome of the *E. coli* MG1655/pKD46 in place of the ptsHI-crr operon by the method described by Datsenko K. A. and Wanner B. L. (Proc. Natl. Acad. Sci. USA, 2000, 97, 6640-6645) which is also called as a "Red-mediated integration" and/or "Red-driven integration", also described in Example 1.

The ptsHI-crr operon has been elucidated (nucleotide numbers 2531786 to 2532043, 2532088 to 2533815 and 2533856 to 2534365 for ptsH, ptsI and crr genes, respectively, in the sequence of GenBank accession NC_000913.2, gi: 49175990). The ptsHI-crr operon is located between cysK and pdxK genes on the chromosome of *E. coli* K-12.

A DNA fragment carrying the $Km^R$ gene was obtained by PCR using the commercially available plasmid pUC4KAN (GenBank/EMBL accession number X06404, "Fermentas", Lithuania) as the template and primers P6 (SEQ ID NO: 9) and P7 (SEQ ID NO: 10). Primer P6 contains 36 nucleotides homologous to the 5'-terminus of the ptsH gene and primer P7 contains 36 nucleotides homologous to the 3'-terminus of the crr gene. These sequences were introduced into primers P6 and P7 for further integration into the bacterial chromosome.

PCR was conducted as described in Example 1.

Then, the amplified DNA fragment was concentrated by agarose gel-electrophoresis, extracted from the gel by the centrifugation through "GenElute Spin Columns" ("Sigma", USA) and precipitated by ethanol. The obtained DNA fragment was used for electroporation and Red-mediated integration into the bacterial chromosome of the *E. coli* MG1655/pKD46 as described in Example 1, except that cells were spread after electroporation onto L-agar containing 50 μg/ml of kanamycin.

Colonies grown within 24 hours were tested for the presence of $Km^R$ marker instead of ptsHI-crr operon by PCR using primers P8 (SEQ ID NO: 11) and P9 (SEQ ID NO: 12). For this purpose, a freshly isolated colony was suspended in 20 μl water and then 1 μl of the resulting suspension was used for PCR. PCR conditions were as described in Example 1. A few $Km^R$ colonies tested contained the desired ~1300 bp DNA fragment, which confirmed the presence of $Km^R$ gene in the place of the ptsHI-crr operon. One of the obtained strains was cured from thermosensitive plasmid pKD46 by culturing at 37° C. and the resulting strain was named *E. coli* MG1655 ΔptsHI-crr.

Then, the DNA fragment from the chromosome of the above-mentioned *E. coli* MG1655$P_{L-tac}$xylE was transferred to *E. coli* MG1655 ΔptsHI-crr by P1 transduction (Miller, J. H. (1972) Experiments in Molecular Genetics, Cold Spring Harbor Lab. Press, Plainview, N.Y.) giving the strain MG1655 ΔptsHI-crr $P_{L-tac}$xylE.

Figure 2:
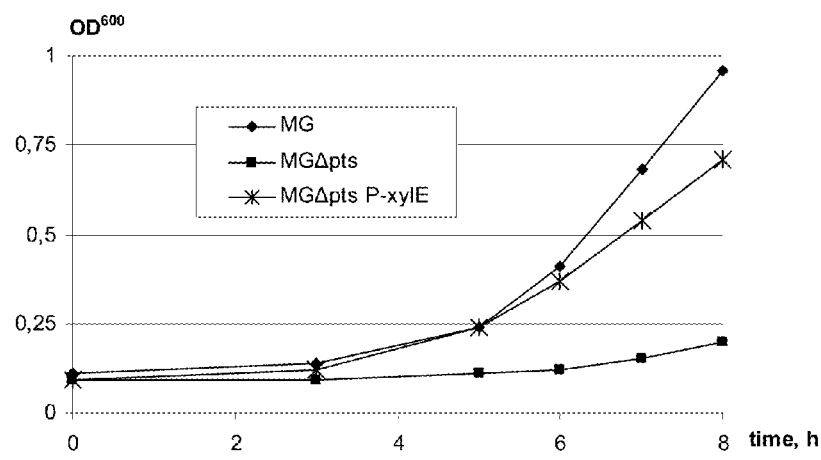
FIG. 2 shows growth curves of E. coli strains MG1655, MG1655 ΔptsHI-crr and MG1655$P_{L-tac}$xylE grown on medium with glucose. Legend: MG=E. coli MG1655; MG Δpts=E. coli MG1655 ΔptsHI-crr; MG Δpts P xylE=E. coli MG1655 ΔptsHI-crr$P_{L-tac}$xylE.

The ability to grow on the minimal Adams with glucose (4%) as a carbon source was checked for the four *E. coli* strains MG1655, MG1655 ΔptsHI-crr and MG1655 ΔptsHI-crr $P_{L-tac}$xylE. As seen in FIG. 2, *E. coli* MG1655 ΔptsHI-crr did not grow well (μ~0.06) on the minimal Adams medium containing glucose. Increasing the xylE gene expression significantly enhanced the growing characteristics of recipient strains on the minimal Adams medium containing glucose.

Example 3

Effect of Increasing the xylE Gene Expression on Threonine Production

To test the effect of enhanced expression of the xylE gene which is under the control of $P_{L-tac}$ promoter on threonine production, DNA fragments from the chromosome of the above-described *E. coli* MG1655$P_{L-tac}$XylE were transferred to the threonine-producing *E. coli* strain VKPM B-3996 by P1 transduction (Miller, J. H. (1972) Experiments in Molecular Genetics, Cold Spring Harbor Lab. Press, Plainview, N.Y.). The strain VKPM B-3996 was deposited in Russian National Collection of Industrial Microorganisms (VKPM) (Russia, 117545 Moscow, 1$^{st}$ Dorozhny proezd, 1) on Apr. 7, 1987 under the accession number B-3996.

Both *E. coli* strains B-3996 and B-3996$P_{L-tac}$XylE were grown for 18-24 hours at 37° C. on L-agar plates. To obtain a seed culture, the strain was grown on a rotary shaker (250 rpm) at 32° C. for 18 hours in 20×200 mm test tubes containing 2 ml of L-broth with 4% sucrose. Then, the fermentation medium was inoculated with 0.21 ml (10%) seed material. The fermentation was performed in 2 ml of minimal medium for fermentation in 20×200 mm test tubes. Cells were grown for 48 hours at 32° C. with shaking at 250 rpm.

After cultivation, the amount of accumulated L-threonine in the medium was determined by paper chromatography using following mobile phase:butanol:acetic acid:water=4: 1:1 (v/v). A solution (2%) of ninhydrin in acetone was used as a visualizing reagent. A spot containing L-threonine was cut off, L-threonine was eluted in 0.5% water solution of $CdCl_2$, and the amount of L-threonine was estimated spectrophotometrically at 540 nm. The results are presented in Table 1. Threonine production was improved due to introduction of $P_{L-tac}$xylE.

The composition of the fermentation medium (g/l) is as follows:

| | |
|---|---|
| Glucose | 80.0 |
| $(NH_4)_2SO_4$ | 22.0 |
| NaCl | 0.8 |
| $KH_2PO_4$ | 2.0 |
| $MgSO_4$ $7H_2O$ | 0.8 |
| $FeSO_4$ $7H_2O$ | 0.02 |
| $MnSO_4$ $5H_2O$ | 0.02 |
| Thiamine HCl | 0.0002 |
| Yeast extract | 1.0 |
| $CaCO_3$ | 30.0 |

Glucose and magnesium sulfate are sterilized separately. CaCO$_3$ is dry-heat sterilized at 180° C. for 2 hours. The pH is adjusted to 7.0. Antibiotic is introduced into the medium after sterilization.

Example 4

Effect of Increasing the xylE Gene Expression on L-Lysine Production

The whole nucleotide sequence of the chromosomal DNA of *E. coli* W3110 is already known (Science, 277, 1453-1474 (1997)). Based on the reported nucleotide sequence, primers were synthesized and the xylE gene was amplified by the PCR method as follows.

The chromosomal DNA was prepared by the conventional method (Sambrook, J., Fritsch E. F. and Maniatis T. (1989): Molecular Cloning: A laboratory manual, 2nd ed. Cold Spring Harbor Laboratory Press, Cold Spring Harbor, N.Y.). The primer 10 (SEQ ID NO: 13) was designed as a sequence in which an EcoRI recognition site is added to the 5'-terminal of the sequence 7479-7508 of the accession No. AE000476, and the primer 11 (SEQ ID NO: 14) was designed as a sequence complementary to the sequence in which a SalI recognition site is added to the 5'-terminal of the sequence 8963-8992 of the accession No. AE000476. By using these primers, the xylE gene was amplified according to the standard conditions as described in "PCR protocols. Current methods and applications" (White, B. A., ed., Humana Press, Totowa, N.J., 1993).

The PCR product was purified by a conventional method. The product was digested with restriction enzymes SalI and EcoRI, and using a ligation kit, ligated to the vector pSTV29 which had been treated with the same restriction enzymes. Competent cells of *E. coli* JM109 were transformed with the ligation product (Sambrook, J., Fritsch E. F. and Maniatis T. (1989) Molecular Cloning: A laboratory manual, 2nd ed. Cold Spring Harbor Laboratory Press, Cold Spring Harbor, N.Y.), and the cells were plated on an L-plate (Bacto-trypton: 10 g/l, yeast extract: 5 g/l, NaCl: 5 g/l, agar: 15 g/l, pH 7.0) containing 10 μg/ml of IPTG (isopropyl-β-D-thiogalactopyranoside), 40 μg/ml of X-Gal (5-bromo-4-chloro-3-indolyl-β-D-galactoside) and 50 μg/ml of chloramphenicol and were cultured overnight. White colonies appeared and were picked up and isolated, and transformants were thus obtained. Plasmids were prepared from the transformants by the alkaliextraction method, and the plasmid pSTV29-xylE was obtained in which the xylE gene is linked to the lac promoter in the forward direction.

*E. coli* WC196 was used as an L-lysine producing strain belonging to the genus *Escherichia*.

WC196 was transformed with either the plasmid pSTV29-xylE or the vector pSTV29 and WC196/pSTV29-xylE and WC196/pSTV29 were obtained. Each of these strains was cultured in the L-medium containing 50 mg/l of chloramphenicol at 37° C. until the final OD at 600 nm reached around 0.6. Then an equal volume of 40% glycerol solution was added to the culture, and the mixture was dispensed in an appropriate volume and stocked at −80° C. This is hereafter called as a "glycerol stock".

In order to verify the effect of enhancing the xylose permease activity under L-lysine producing conditions, WC196 was transformed with the plasmids pSTV29-xylE and pCABD2 in accordance with the procedure as stated above. pCABD2 is a plasmid comprising a dapA gene coding for a dihydrodipicolinate synthase having a mutation which desensitizes feedback inhibition by L-lysine, a lysC gene coding for aspartokinase III having a mutation which desensitizes feedback inhibition by L-lysine, a dapB gene coding for a dihydrodipicolinate reductase gene, and a ddh gene coding for diaminopimelate dehydrogenase (U.S. Pat. No. 6,040,160). As a control, WC196 was transformed with the plasmids pSTV29 and pCABD2. Each of the obtained transformants was cultured in the L-medium containing 50 mg/l of chloramphenicol and 20 mg/l of streptomycin at 37° C. until the final OD at 600 nm reached around 0.6. Then an equal volume of 40% glycerol solution was added to the culture, and the mixture was dispensed in an appropriate volume and stocked at −80° C.

The glycerol stock of each of WC196/pSTV29-xylE and WC196/pSTV29 was melted and 100 μl each was evenly plated on an L-plate containing 50 mg/l of chloramphenicol, and cultured at 37° C. for 24 hours. In addition, each of WC196/(pCABD2, pSTV29-xylE) and WC196/(pCABD2, pSTV29) was evenly plated on an L-plate containing 50 mg/l of chloramphenicol and 20 mg/l of streptomycin, and cultured at 37° C. for 24 hours. About one-eighth the amount of cells on the plate was inoculated into 20 ml of the fermentation medium containing the required drug(s) in a 500 ml-flask. The cultivation was carried out at 37° C. for 16 hours by using a reciprocal shaker at the agitation speed of 115 rpm. After the cultivation, the amounts of L-lysine and residual glucose in the medium were measured by a known method (Biotech-analyzer AS210, manufactured by Sakura Seiki Co.). And then the yield of L-lysine relative to the consumed glucose was calculated for each of the strains.

The composition of the fermentation medium (g/l) is as follows:

| | |
|---|---|
| Glucose | 40 |
| (NH$_4$)$_2$SO$_4$ | 24 |
| K$_2$HPO$_4$ | 1.0 |
| MgSO$_4$ × 7H$_2$O | 1.0 |
| FeSO$_4$ × 7H$_2$O | 0.01 |
| MnSO$_4$ × 5H$_2$O | 0.01 |
| Yeast extract | 2.0 | pH is adjusted to 7.0 by KOH and the medium is autoclaved at 115° C. for 10 min. Glucose and MgSO$_4$×7H$_2$O are sterilized separately. 30 g/l of CaCO$_3$, which has been dry-heat sterilized at 180° C. for 2 hours, is added.

The results are shown in Table 2. WC196/pSTV29-xylE accumulated a higher amount of L-lysine as compared with WC196/pSTV29, in which the expression amount of xylose permease is not increased. In addition, it was observed that enhancing the xylose permease activity improves the accumulation and yield of L-lysine also in WC196/pCABD2, which produces L-lysine in a higher amount.

Example 5

Effect of the Increasing the xylE Gene Expression on L-Arginine Production

To test the effect of enhanced expression of the xylE gene which is under the control of P$_{L-tac}$ promoter on arginine production, DNA fragments from the chromosome of the above-described *E. coli* MG1655P$_{L-tac}$xylE were transferred to the arginine-producing *E. coli* strain 382 by P1 transduction (Miller, J. H. (1972) Experiments in Molecular Genetics, Cold Spring Harbor Lab. Press, Plainview, N.Y.). The strain 382 has been deposited in the Russian National Collection of Industrial Microorganisms (VKPM) (Russia, 117545 Moscow, 1$^{st}$ Dorozhny proezd, 1) on Apr. 10, 2000 under accession number VKPM B-7926.

The resulting strain 382 P$_{L-tac}$xylE and parent strain 382 were each cultivated at 32° C. for 18 hours in 2 ml of LB nutrient broth, and 0.3 ml of the obtained culture was inoculated into 2 ml of fermentation medium in a 20×200 mm test tube, and cultivated at 32° C. for 48 hours on a rotary shaker.

After the cultivation, the amount of L-arginine accumulated in the medium was determined by paper chromatography using following mobile phase:butanol:acetic acid:water=4:1:1 (v/v). A solution (2%) of ninhydrin in acetone was used as a visualizing reagent. A spot containing L-arginine was cut off, L-arginine was eluted in 0.5% water solution of CdCl$_2$, and the amount of L-arginine was estimated spectrophotometrically at 540 nm.

The composition of the fermentation medium (g/l) is as follows:

| | |
|---|---|
| Glucose | 48.0 |
| (NH4)$_2$SO$_4$ | 35.0 |
| KH$_2$PO$_4$ | 2.0 |
| MgSO$_4$ × 7H$_2$O | 1.0 |
| Thiamine HCl | 0.0002 |
| Yeast extract | 1.0 |
| L-isoleucine | 0.1 |
| CaCO3 | 5.0 |

Glucose and magnesium sulfate are sterilized separately. CaCO$_3$ is dry-heat sterilized at 180° C. for 2 hours. pH is adjusted to 7.0.

The results of 10 independent experiments are presented in Table 3. It can be seen from the Table 3, strain 382 P$_{L-tac}$XylE accumulated a higher amount of L-arginine as compared with strain 382, in which the expression amount of D-xylose permease is not increased.

Example 6

Production of L-Histidine by L-Histidine Producing Bacterium from Fermentation of a Mixture of Glucose and Xylose The L-histidine-producing *E. coli* strain 80 was used for production of L-histidine by fermentation of a mixture of glucose and xylose. *E. coli* strain 80 (VKPM B-7270) is described in detail in Russian patent RU2119536.

To test the effect on histidine production of enhanced expression of the xylE gene which is under the control of P$_{L-tac}$ promoter, the DNA fragments from the chromosome of the above-described *E. coli* MG1655P$_{L-tac}$xylE were transferred to histidine-producing *E. coli* strain 80 by P1 transduction (Miller, J. H. (1972) Experiments in Molecular Genetics, Cold Spring Harbor Lab. Press, Plainview, N.Y.). Transformation of strain 80 and the resulting strain 80 P$_{L-tac}$XylE with the pMW119mod-xylA-R plasmid was performed by ordinary methods, yielding strains 80/pMW119mod-xylA-R and 80 P$_{L-tac}$xylE/pMW119mod-xylA-R. Cloning of the xylABFGHR locus from the chromosome of *E. coli* strain MG1655 is described in the Russian patent application RU2005106720.

To obtain the seed culture, both strains 80/pMW119mod-xylA-R and 80 P$_{L-tac}$XylE/pMW119mod-xylA-R, were grown on a rotary shaker (250 rpm) at 27° C. for 6 hours in 40 ml test tubes (Ø18 mm) containing 2 ml of L-broth with 1 g/l of streptomycin and 100 mg/l ampicillin. Then, 2 ml (5%) of seed material was inoculated into the fermentation medium. Fermentation was carried out on a rotary shaker (250 rpm) at 27° C. for 50 hours in 40 ml test tubes containing 2 ml of fermentation medium.

After cultivation, the amount of L-histidine which had accumulated in the culture medium was determined by paper chromatography. The composition of the mobile phase is the following: butanol:acetate:water=4:1:1 (v/v). A solution (0.5%) of ninhydrin in acetone was used as a visualizing reagent. The results are presented in Table 4.

The composition of the fermentation medium (g/l) is as follows:

| | |
|---|---|
| Carbohydrates (total) | 100.0 |
| Mameno (Soybean hydrolysate) | 0.2 of total nitrogen |
| L-proline | 0.8 |
| (NH$_4$)$_2$SO$_4$ | 25.0 |
| K$_2$HPO$_4$ | 2.0 |
| MgSO$_4$ × 7H$_2$O | 1.0 |
| FeSO$_4$ × 7H$_2$O | 0.01 |
| MnSO$_4$ × 5H$_2$O | 0.01 |
| Thiamine HCl | 0.001 |
| Betaine | 2.0 |
| CaCO$_3$ | 6.0 |
| Streptomycin | 1.0 |

Carbohydrates (glucose, xylose), L-proline, betaine and magnesium sulfate are sterilized separately. CaCO$_3$ is dry-heat sterilized at 110° C. for 30 min. pH is adjusted to 6.0 by KOH before sterilization.

It can be seen from Table 4 that strain 80 P$_{L-tac}$XylE/pMW119mod-xylA-R caused accumulation of a higher amount of L-histidine in the medium containing glucose and xylose mixture as compared with strain 80/pMW119mod-xylA-R, in which the expression of D-xylose permease is not increased.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

TABLE 1

| Strain | OD$_{540}$ | Threonine, g/l |
|---|---|---|
| B3996P$_{L-tac}$xylE | 21.6 | 26.9 |
| | 19.5 | 24.0 |
| | 21.3 | 25.9 |
| | 23.4 | 26.4 |
| | 19.7 | 24.6 |
| | 22.0 | 29.4 |
| | 18.9 | 28.4 |
| | 20.0 | 25.9 |
| | 22.6 | 26.4 |
| | 20.8 | 27.1 |
| | 20.5 | 26.9 |
| | 19.5 | 25.9 |
| | 19.5 | 25.4 |
| | 20.2 | 23.6 |
| | 20.7 | 28.7 |
| | 20.2 | 28.9 |
| | 19.4 | 29.2 |
| | 20.5 | 29.0 |
| | 20.2 | 29.5 |
| | 20.5 | 29.2 |
| | 20.6 ± 1.1 | 27.1 ± 1.9 |
| B-3996 (control) | 16.5 | 21.0 |
| | 16.0 | 19.8 |
| | 16.0 | 19.0 |
| | 14.4 | 17.5 |
| | 15.5 | 19.0 |
| | 14.7 | 18.7 |

TABLE 1-continued

| Strain | OD$_{540}$ | Threonine, g/l |
|---|---|---|
| | 16.6 | 20.6 |
| | 16.5 | 21.0 |
| | 14.7 | 16.0 |
| | 15.7 | 20.3 |
| | 15.7 ± 0.8 | 19.3 ± 1.6 |

TABLE 2

| Strain | L-Lysine HCl, g/l | Yield from glucose (%) |
|---|---|---|
| WC196/pSTV29 | 0.5 | 2.3 |
| WC196/pSTV29-xylE | 1.0 | 3.5 |
| WC196/pCABD2, pSTV29 | 1.8 | 32.4 |
| WC196/pCABD2, pSTV29-xylE | 4.0 | 38.7 |

TABLE 3

| Strain | OD$_{540}$ | Arginine, g/l |
|---|---|---|
| 382 | 17.0 | 4.9 |
| | 16.8 | 4.6 |
| | 16.8 | 4.9 |
| | 19.5 | 6.2 |
| | 21.1 | 5.3 |
| | 16.3 | 4.7 |
| | 16.1 | 4.6 |
| | 17.1 | 4.6 |
| | 17.6 | 4.9 |

TABLE 3-continued

| Strain | OD$_{540}$ | Arginine, g/l |
|---|---|---|
| | 17.0 | 4.7 |
| | 17.5 ± 1.6 | 4.9 ± 0.5 |
| 382 P$_{L\text{-}tac}$xylE | 18.0 | 9.6 |
| | 17.8 | 11.9 |
| | 20.3 | 7.4 |
| | 19.2 | 8.6 |
| | 21.3 | 7.7 |
| | 20.1 | 7.0 |
| | 19.7 | 6.6 |
| | 20.6 | 7.6 |
| | 20.0 | 6.9 |
| | 20.6 | 8.4 |
| | 19.8 ± 1.1 | 8.2 ± 1.6 |

TABLE 4

| Strain | CT, hours | Growth, A$_{450}$ | Residual glucose, % | Residual xylose, % | Amount of histidine, g/l |
|---|---|---|---|---|---|
| 80/pMW119mod-xylA-R | 0 | — | 100 | 100 | — |
| | 16 | 15 | 85.6 | 92.3 | 0.3 + 0.01 |
| | 24 | 48 | 44.3 | 79.8 | 1.1 + 0.08 |
| | 40 | 67 | 0.86 | 14.7 | 5.9 + 0.05 |
| | 48 | 66 | <0.5 | 0.7 | 6.5 + 0.3 |
| 80 P$_{L\text{-}tac}$XylE/ pMW119mod-xylA-R | 0 | — | 100 | 100 | — |
| | 16 | 15 | 90.9 | 89.3 | 0.3 + 0.01 |
| | 24 | 25 | 78.6 | 72.9 | 0.7 + 0.03 |
| | 40 | 69 | 26.3 | <0.5 | 6.3 + 0.3 |
| | 48 | 66 | 2.5 | <0.5 | 7.4 + 0.3 |

We claim:

1. A method for producing L-amino acid, which comprises cultivating a bacterium of Enterobacteriaceae family in a culture medium to cause accumulation of the L-amino acid in the culture medium, and isolating the L-amino acid from the culture medium, wherein said bacterium has been modified to enhance an activity of D-xylose permease and activities of xylose utilization proteins encoded by xylABFGHR locus by a method selected from the group consisting of:
   a) increasing the copy number of a gene encoding D-xylose permease and the xylABFGHR locus,
   b) placing the gene encoding D-xylose permease and the xylABFGHR locus under the control of a potent promoter, and
   c) combinations thereof,
   wherein the carbon source in said culture medium consists of glucose; and
   wherein said D-xylose permease and said xylose utilization proteins encoded by xylABFGHR locus are both derived from a bacteria of the Enterobacteriaceae family.

2. The method according to claim 1, wherein said gene encoding D-xylose permease is selected from the group consisting of:
   (A) a protein comprising the amino acid sequence of SEQ ID NO:2; and
   (B) a protein comprising an amino acid sequence which is at least 95% homologous to the sequence of SEQ ID NO:2 and has an activity of D-xylose permease.

3. The method according to claim 1, wherein said gene encoding D-xylose permease is selected from the group consisting of:
   a) a DNA comprising nucleotides 1 to 1476 in SEQ ID NO:1; and
   b) a DNA which is hybridizable with nucleotides 1 to 1476 in SEQ ID NO:1 under stringent conditions comprising washing at 60° C. at a salt concentration of 1×SSC and 0.1% SDS for 15 minutes, and said DNA encodes a protein having an activity of D-xylose permease.

4. The method according to claim 1, wherein said bacterium is an L-threonine producing bacterium.

5. The method according to claim 4, wherein said bacterium has been additionally modified to enhance expression of a gene selected from the group consisting of
   the mutant thrA gene which codes for aspartokinase homoserine dehydrogenase I and is resistant to feedback inhibition by threonine,
   the thrB gene which codes for homoserine kinase,
   the thrC gene which codes for threonine synthase,
   the rhtA gene which codes for a putative transmembrane protein, and
   combinations thereof.

6. The method according to claim 5, wherein said bacterium has been modified to increase expression of said mutant thrA gene, said thrB gene, said thrC gene, and said rhtA gene.

7. The method according to claim 1, wherein said bacterium is *Escherichia coli*.

8. The method according to claim 1, wherein said bacterium is *Pantoea ananatis*.

* * * * *